US005861495A

United States Patent [19]
Hillman et al.

[11] Patent Number: 5,861,495
[45] Date of Patent: Jan. 19, 1999

[54] HUMAN ZINC BINDING PROTEINS

[75] Inventors: Jennifer L. Hillman; Janice Au-Young; Roger Coleman; Surya K. Goli, all of Palo Alto, Calif.

[73] Assignee: Incyte Pharmaceuticals, Inc., Palo Alto, Calif.

[21] Appl. No.: 786,606

[22] Filed: Jan. 21, 1997

[51] Int. Cl.$^6$ .............................. C07H 21/02; C07H 21/04
[52] U.S. Cl. ..................... 536/23.1; 536/23.5; 530/350; 435/69.1; 435/69.3; 435/71.1; 435/320.1; 435/273; 435/257.3
[58] Field of Search ................................ 514/44; 436/518; 435/5, 69.1, 69.3, 71.1, 320.1, 273, 252.3; 536/23.1, 23.5; 530/350, 380; 935/22, 66–75

[56] References Cited

PUBLICATIONS

Berg, J., et al., "The Galvanization of Biology: A Growing Appreciation for the Roles of Zinc," *Science*, 271:1081–1085 (1996).
Hanas, J., et al., "Xenopus Transcription Factor A Requires Zinc for Binding to the 5 S RNA Gene," *The Journal of Biological Chemistry*, 258(23):14120–14125 (1983).
Shi, Y., et al., "Specific DNA–RNA Hybrid Binding by Zinc Finger Proteins," *Science*, 268:282–284 (1995) (GI 120625).
McGrew, L. et al., "Poly(A) elongation during Xenopus oocyte maturation is required for translational recruitment and is mediated by a short sequence element," *Genes & Development*, 3:803–815 (1989).
Benit, P., et al., "Yeast Sequencing Reports," *Yeast*, 8:147–153 (1992).
Lovering, R., et al., "Identification and preliminary characterization of a protein motif related to the zinc finger," *Proc. Natl. Acad. Sci. USA*, 90:2112–2116 (1993).
Barlow, P., et al., "Structure of the C3HC4 Domain by H–nuclear Magnetic Resonance Spectroscopy," *J. Mol. Biol.*, 237:201–211 (1994).
Haupt, Y., et al., "Novel Zinc Finger Gene Implicated as myc Collaborator by Retrovirally Accelerated Lymphomagenesis in Eμ–myc Transgenic Mice," *Cell*, 65:753–763 (1991).
Alkema, M., et al., "Characterization and chromosomal localization of the human proto–oncogene BMI–1," *Human Molecular Genetics*, 2(10):1597–1603 (1993) (GI 461632).
Thompson, M., et al., "Decreased expression of BRCA1 accelerates growth and is often present during sporadic breast cancer progression," *Nature Genetics*, 9:444–450 (1995).
Bouchard, M., et al., "The *Drosophila melanogasteri* developmental gene g1 encodes a variant zinc–finger–motif protein," *Gene*, 125:205–209 (1993) (GI 157535).
Mitchell, P., et al., "Transcriptional Regulation in Mammalian Cells by Sequence–Specific DNA Binding Proteins," *Science*, 245:371–378 (1989).
Hla, T., et al., "Characterization of edg–2, a human homologue of the Xenopus maternal transcript G10 from endothelial cells," *Biochimica et Biophysica Acta*, 1260:227–229 (1995).

*Primary Examiner*—Sheela Huff
*Attorney, Agent, or Firm*—Lucy J. Billings; Sheela Mohan-Peterson; Incyte Pharmaceuticals, Inc.

[57] ABSTRACT

The present invention provides three zinc binding proteins (designated individually as ZB-1, ZB-2, and ZB-3, and collectively as ZB) and polynucleotides which identify and encode ZB. The invention also provides genetically engineered expression vectors and host cells comprising the nucleic acid sequences encoding ZB and a method for producing ZB. The invention also provides for use of ZB and agonists, antibodies, or antagonists specifically binding ZB, in the prevention and treatment of diseases associated with expression of ZB. Additionally, the invention provides for the use of antisense molecules to polynucleotides encoding ZB for the treatment of diseases associated with the expression of ZB. The invention also provides diagnostic assays which utilize the polynucleotide, or fragments or the complement thereof, and antibodies specifically binding ZB.

8 Claims, 22 Drawing Sheets

```
5'
   G CCT GAA GAG CGG AAG CCT TCT GTC GAG AAG CAG CTA CCC AAG CTC CAG GAG
     63              72              81              90              99             108
   CTT CCG AAA CAG GAC CAG AGA GGG AAG GTG ACC TGA AAG TCA CAG AAT AAT
    117             126             135             144             153             162
   TTT TTA GAG CTG AAC AAG AAT CCA AGC CTG CAA CTG CAG AGA CGA GAG ATC TTT
    171             180             189             198             207             216
   CTG CTG TCT ATA CTC TTG GAA AGC ACA TCC TAA GAT CTT TGC AGA TTA TCC TGT
    225             234             243             252             261             270
   GGA AGG AAA ATG CCT AAA GTC AAA AGA AGC CGG AAA GCA CCC CCA GAT GGC TGG
                    M   P   K   V   K   R   S   R   K   A   P   P   D   G   W
    279             288             297             306             315             324
   GAG TTG ATT GAG CCA ACA CTG GAT GAA TTA CAA AAG ATG AGA GAA GCT GAA
    E   L   I   E   P   T   L   D   E   L   Q   K   M   R   E   A   E
    333             342             351             360             369             378
   ACA GAA CCG CAT GAG GGA AAG AGG AAA GTG GAA TCT CTG TGG CCC ATC TTC AGG
    T   E   P   H   E   G   K   R   K   V   E   S   L   W   P   I   F   R
    387             396             405             414             423             432
   ATC CAC CAG AAA CGC TAC ATC TTC GAC CTC TTT TAC AAG CGG AAA GCC
    I   H   Q   K   R   Y   I   F   D   L   F   Y   K   R   K   A
    441             450             459             468             477             486
   ATC AGC AGA GAA CTC TAT GAA TAT TGT ATT AAA GAA GGC TAT GCA GAC AAA AAC
    I   S   R   E   L   Y   E   Y   C   I   K   E   G   Y   A   D   K   N
```

```
     495         504         513         522         531         540
CTG ATT GCA AAA TGG AAA AAG CAA GGA TAT GAG AAC TTG TGC CTG CGG TGC
 L   I   A   K   W   K   K   Q   G   Y   E   N   L   C   L   R   C 549         558         567         576         585         594
ATT CAG ACA CGG GAC ACC AAC TTC GGG ACG AAC TGC CGC GTG CCC AAA
 I   Q   T   R   D   T   N   F   G   T   N   C   R   V   P   K 603         612         621         630         639         648
AGC AAG CTG GAA GTG GGC CGC ATC GAG TGC ACA CAC TGT GGC TGT CGT GGC
 S   K   L   E   V   G   R   I   E   C   T   H   C   G   C   R   G 657         666         675         684         693         702
TGC TCT GGC TGA GGC GCT CCA CCC TGG CGC ACT CTG GAC TTC GCA GGT TCC
 C   S   G 711         720         729         738         747         756
TGC CTG TCA CGC CAC CCC CTT CCT GGG AGC AGC GAG CAG TGC CCC AGG CCC GAG 765         774         783         792         801         810
TTG GAG CAC GGT CTC TAT GGG GAA GGC TTC GCT GTC TAT CAG CTG TGA TTT GTA 819         828
AAA ATA AAA TCT TTA AAT CT 3'
```

```
5'  C AAC GAT CGT GGG CAG GAG GTG GTT TCT GGT GTG TTG GGG CGT GTG TAT GTG
                                                                        54
    TAT TTG GGG GGA CTG AAG GGT ACG TGG GGC GAA ACA AAA CCG GCC ATG GCA GCA
                63                     81          90          99    M  A  A  108

GCG GAG GAG GAC CAG GGG CCC GAA GGG CCA AAT CGC GAG CGG GGC GGG GCG
     A   E   E   D   Q   G   P   E   G   P   N   R   E   R   G   G   A  162
        117                 126         135         144         153

GGC GCG ACC TTC GAA TGT AAT ATA TGT TTG GAG ACT GCT CGG GAA GCT GTG GTC
     G   A   T   F   E   C   N   I   C   L   E   T   A   R   E   A   V   V  216
        171                 180         189         198         207

AGT GTG TGT GGC CAC CTG TAC TGT TGG CCA TGT CTT CAT CAG TGG CTG GAG ACA
     S   V   C   G   H   L   Y   C   W   P   C   L   H   Q   W   L   E   T  270
        225                 234         243         252         261

CGG CCA GAA CGG CAA GAG TGT CCA GTA TGT AAA GCT GGG ATC AGC AGA GAG AAG
     R   P   E   R   Q   E   C   P   V   C   K   A   G   I   S   R   E   K  324
        279                 288         297         306         315

GTT GTC CCG CTT TAT GGG CGA GGG AGC CAG AAG CCC CAG GAT CCC AGA TTA AAA
     V   V   P   L   Y   G   R   G   S   Q   K   P   Q   D   P   R   L   K  378
        333                 342         351         360         369

FIGURE 2A
```

```
     387      396      405      414      423      432
ACT CCA CCC CGC CCC CAG GGC CAG AGA CCA GCT CCG GAG AGC AGA GGG GGA TTC
 T   P   P   R   P   Q   G   Q   R   P   A   P   E   S   R   G   G   F 441      450      459      468      477      486
CAG CCA TTT GGT GAT ACC GGG GGC TTC CAC TTC TCA TTT GGT GTT GGT GCT TTT
 Q   P   F   G   D   T   G   G   F   H   F   S   F   G   V   G   A   F 495      504      513      522      531      540
CCC TTT GGC TTT TTC ACC GTC ACC TTC AAT GCC CAT GAG CCT TTC CGC CGG GGT
 P   F   G   F   F   T   V   T   F   N   A   H   E   P   F   R   R   G 549      558      567      576      585      594
ACA GGT GTG GAT CTG GGA CAG GGT CAC CCA GCC TCC AGC TGG CAG GAT TCC CTC
 T   G   V   D   L   G   Q   G   H   P   A   S   S   W   Q   D   S   L 603      612      621      630      639      648
TTC CTG TTT CTC GCC ATC TTC TTC TTT TTT TGG CTG CTC AGT ATT TGA GCT ATG
 F   L   F   L   A   I   F   F   F   F   W   L   L   S   I 657      666      675      684      693      702
TCT GCT TCC TGC CCA CCT CCA GCC AGA GAA GAA TCA GTA TAT TGA AGG TCC CTG 711      720      729      738      747      756
CTG AMC CTT CCG TAT CCT GGA ACC CCT GAC CCT TTT TTT TTG CTA ANG GCA
```

FIGURE 2B

```
       765           774           783           792           801           810
CCC TGA ACT TTT CCN GAA GGC TGG GAA AAA ATT AAT CTT TCT TAA TGG AAA NCT 819           828           837           846           855           864
CTC CCC AAG NCC TCA TAA CTT TTT AAT CCC CCC NGG GAA GAG ATG AAT AAA AAA 873           882           891           900           909           918
TTN TTC NCC CCC AAT TTT GCT TCC CGA TTC TNA TTN ACT CAA GTG GCA ATT CCC 927           936           945
TNA TCT CCC CTC CAC TTT GAT AAT TAT T 3'
```

FIGURE 2C

```
                                                9                18               27               36               45               54
5'  GNC GCT AAC GGG CTT GAN TCC CCC AAG GCC GAG GTC CGC GGC CAG GTG CTG GCG 63               72               81               90               99              108
    CCG CTG CCC CTC CAC CGA GTT GCT GAT CAT CTG GCT GAT CTG GGC TGT GAT CCA CAA ACC CGG 117              126              135              144              153              162
    TTC TTT GTC CCT CCT AAT ATC AAA CAG TGG ATT GCC TTG CTG CAG AGG GGA AAC 171              180              189              198              207              216
    TGC ACG TTT AAA GAG AAA ATA TCA CGG GCC GCT TTC CAC AAT GCA GTT GCT GTA 225              234              243              252              261              270
    GTC ATC TAC AAT AAT AAA TCC AAA GAG GAG CCA GTT ACC ATG ACT CAT CCA GGC
                                                                    M   T   H   P   G 279              288              297              306              315              324
    ACT GGA GAT ATT ATT GCT GTC ATG ATA ACA GAA TTG AGG GGT AAG GAT ATT TTG
     T   G   D   I   I   A   V   M   I   T   E   L   R   G   K   D   I   L 333              342              351              360              369              378
    AGT TAT CTG GAG AAA AAC ATC TCT GTA CAA ATG ACA ATA GCT GTT GGA ACT CGA
     S   Y   L   E   K   N   I   S   V   Q   M   T   I   A   V   G   T   R
```

FIGURE 3A

| | 387 | 396 | 405 | 414 | 423 | 432 |
|---|---|---|---|---|---|---|
| ATG | CCA | AAG | AAC | TTC | AGC | CGT | GGC | TCT | CTA | TCT | GTC | TTC | TCA | ATA | TCC | TTT |
| M | P | K | N | F | S | R | G | S | L | V | F | S | I | S | F |

| | 441 | 450 | 459 | 468 | 477 | 486 |
|---|---|---|---|---|---|---|
| ATT | GTT | TTG | ATG | ATT | TCT | TCA | GCA | TGG | CTC | ATA | TTC | TAC | TTC | ATT | CAG | AAG |
| I | V | L | M | I | S | S | A | W | L | I | F | Y | F | I | Q | K |

| | 495 | 504 | 513 | 522 | 531 | 540 |
|---|---|---|---|---|---|---|
| ATC | AGG | TAC | ACA | AAT | GCA | CGC | GAC | AGG | AAC | CAG | CGT | CTC | CGT | GGA | GAT | GCA | GCC |
| I | R | Y | T | N | A | R | D | R | N | Q | R | L | R | G | D | A | A |

| | 549 | 558 | 567 | 576 | 585 | 594 |
|---|---|---|---|---|---|---|
| AAG | AAA | ATC | AGT | GCA | AAA | TTG | ACA | ACC | AGG | ACA | GTA | AAG | AAG | GGT | GAC | AAG | GAA |
| K | K | I | S | A | K | L | T | T | R | T | V | K | K | G | D | K | E |

| | 603 | 612 | 621 | 630 | 639 | 648 |
|---|---|---|---|---|---|---|
| ACT | GAC | CCA | GAC | TTT | GAT | CAT | TGT | GCA | GTC | TGC | ATA | GAG | AGC | TAT | AAG | CAG | AAT |
| T | D | P | D | F | D | H | C | A | V | C | I | E | S | Y | K | Q | N |

| | 657 | 666 | 675 | 684 | 693 | 702 |
|---|---|---|---|---|---|---|
| GAT | GTC | GTC | CGA | ATT | CTC | CCC | TGC | AAG | CAT | GTT | TTC | CAC | AAA | TCC | TGC | GTG | GAT |
| D | V | V | R | I | L | P | C | K | H | V | F | H | K | S | C | V | D |

| | 711 | 720 | 729 | 738 | 747 | 756 |
|---|---|---|---|---|---|---|
| CCC | TGG | CTT | AGT | GAA | CAT | TGT | ACC | TGT | CCT | ATG | TGC | AAA | CTT | AAT | ATA | TTG | AAG |
| P | W | L | S | E | H | C | T | C | P | M | C | K | L | N | I | L | K |

FIGURE 3B

```
       765            774            783            792            801            810
GCC CTG GGA ATT GTG CCG AAT TTG CCA TGT ACT GAT AAC GTA GCA TTC GAT ATG
 A   L   G   I   V   P   N   L   P   C   T   D   N   V   A   F   D   M 819            828            837            846            855            864
GAA AGG CTC ACC AGA ACC CAA GCT GTT AAC CGA AGA TCA GCC CTC GGC GAC CTC
 E   R   L   T   R   T   Q   A   V   N   R   R   S   A   L   G   D   L 873            882            891            900            909            918
GCC GGC GAC AAC TCC CTT GGC CTT GAG CCA CTT CGA ACT TCG GGG ATC TCA CCT
 A   G   D   N   S   L   G   L   E   P   L   R   T   S   G   I   S   P 927            936            945            954            963            972
CTT CCT CAG GAT GGG GAG CTC ACT CCG AGA ACA GGA GAA ATC AAC ATT GCA GTA
 L   P   Q   D   G   E   L   T   P   R   T   G   E   I   N   I   A   V 981            990            999           1008           1017           1026
ACA AAA GAA TGG TTT ATT ATT GCC AGT TTT GGC CTC CTC AGT GCC CTC ACA CTC
 T   K   E   W   F   I   I   A   S   F   G   L   L   S   A   L   T   L 1035           1044           1053           1062           1071           1080
TGC TAC ATG ATC ATC AGA GCC ACA GCT AGC TTG AAT GCT AAT GAG GTA GAA TGG
 C   Y   M   I   I   R   A   T   A   S   L   N   A   N   E   V   E   W 1089           1098           1107           1116           1125           1134
TTT TGA AGA AGA AAA AAC CTG CTT TCT GAC TGA TTT TGC CTT GAA GGA AAA AAG
 F
```

```
1    MAAEEEDGGPEGPNRERGGAGATFECNICLETAREAVVS            134194
1    MHRTTRIKITELNPH-------LMCVLCGGYFIDATTI             GI 461632

41   V-CGHLYCWPCLHQWLETRPEROECPVCKAGISREKVVPL           134194
32   IEDLHSFCKTCIVRYLETS---KYCPICDVQVHKTRPL-L           GI 461632

80   YGRGSQKPQDPRLKTPP--------RPQ--GQRPAPES             134194
68   NIRSDKTLQDIVYKLVPGLFKNEMKRRRDFYAAHPSADAA           GI 461632

108  RGGFQPFGDTGGFHFSF-------GVGAFPFGFFT----            134194
108  NGSNEDRGEVADEDKRIITDDEIISLSIEFDQNRLDRKV            GI 461632

136  ------------------------TVFNAHEPFRRGTGV--          134194
148  NKDKEKSKEEVNDKRYLRCPAAMTVMHLRKFLRSKMDIPN           GI 461632

151  --DLGQGHPASSWQDSLFLAIFFFWL---LSI                   134194
188  TFQIDVMYEEEPLKDYYTLMDIAYIYTWRRNGPLPLKYRV           GI 461632

180                                                     134194
228  RPTCKRMKISHQRDGLTNAGELESDSGSDKANSPAGGVPS           GI 461632

180                                                     134194
268  TSSCLPSPSTPVQSPHPQFPHISSTMNGTSNSPSGNHQSS           GI 461632

180                                                     134194
308  FANRPRKSSVNGSSATSSG                                GI 461632
```

FIGURE 5

```
  1  M- - - - - - THPGTGDIIAVMITELRGKDILSYLEKNISVQM          10773
  1  MQLEKMQIKGKTRNIAAVITYQNIGQDLSLTLDKGYNVTI              GI 157535

35  TIAVGTR- - MPPKNFSRGSLVFVSISFIVLMIISSAWLIF              10773
 41  SIIEGRRGVRTISSLNRTSVLFVSISFIVDDILC- -WLIF             GI 157535

73  YFIQKIRYTNARDRNQRRLGDAAKKAISKLTTRTVKKGDK              10773
 79  YYIQRFRYMQAKDQQSRNLCSVTKKAIMKIPTKTGKFSD-              GI 157535

113  ETDPDFDHCAVCIESYKQNDVVRILPCKHVFHKSCVDPWL              10773
118  EKDLDSDCCAICIEAYKPTDTIRILPCKHEFHKNCIDPWL              GI 157535

153  SEHCTCPMCKLNILKALGIVPNLPCTDNVAFDMERLTRTQ              10773
158  IEHRTCPMCKLDVLKFYGYV- - - - VGDQIYQTPSPQHTA             GI 157535

193  AVNRRSALGDLAGDNSLG- - LEPLRTSGISPLPQDGELT              10773
193  PIASIEEVPVIVVAVPHGPQPLQPLQASNMSFAPSHYF-               GI 157535

230  PRTGEINIAVTKEWFIIASFGLLSALTLCYMIIRATASLN              10773
232  -QSSRSPSSSVQQQLAPLTYQPHPQQAASERGRRRNSAPAT             GI 157535

270  - - - - - -ANEVEWF                                    10773
271  MPHAITASHQVTDV                                       GI 157535
```

FIGURE 6

| Library | Lib Description | Abun | Pct Abun |
|---|---|---|---|
| OVARTUM02 | ovarian tumor, 64 F, WM | 1 | 0.1256 |
| AMLBNOT01 | AML blast cells, blast crisis, 58 F | 1 | 0.1058 |
| BLADNOT04 | bladder and seminal vesicle, 28 M | 3 | 0.0833 |
| HMC1NOT01 | HMC-1 mast cell line, 52 F | 2 | 0.0669 |
| THYRTUT03 | thyroid tumor, benign, 17 M | 2 | 0.0553 |
| BMARNOT02 | bone marrow, 16-70 M/F | 2 | 0.0540 |
| COLNNOT23 | colon, ulcerative colitis, 16 M | 2 | 0.0528 |
| LIVRNOT02 | liver, 32 F | 1 | 0.0517 |
| PROSNOT14 | prostate, 60 M, match to PROSTUT08 | 2 | 0.0512 |
| BLADTUT06 | bladder tumor, carcinoma, 58 M | 1 | 0.0507 |
| THP1PLB02 | THP-1 promonocyte cell line, treated PMA, LPS | 1 | 0.0407 |
| UTRPNOM01 | uterus, F, NORM, WM | 2 | 0.0402 |
| COLNTUT03 | colon tumor, 62 M, match to COLNNOT16 | 2 | 0.0392 |
| MUSCNOT02 | muscle, psoas, 12 M | 1 | 0.0386 |
| BRAITUT03 | brain tumor, astrocytoma, 17 F | 5 | 0.0371 |
| PLACNOM03 | placenta, fetal, NORM, WM | 1 | 0.0363 |
| BRAINOT04 | brain, choroid plexus, hemorrhage, 44 M | 1 | 0.0356 |
| PANCNOT04 | pancreas, 5 M | 2 | 0.0338 |
| MMLR3DT01 | macrophages (adher PBMNC), M/F, 72-hr MLR | 1 | 0.0332 |
| ISLTNOT01 | pancreas, islet cells, M/F | 5 | 0.0322 |
| KIDNNOT05 | kidney, neonatal F | 3 | 0.0317 |
| STOMNOT02 | stomach, 52 M, match to STOMTUT01 | 1 | 0.0308 |
| LUNGFEM01 | lung, fetal, NORM, WM | 2 | 0.0296 |
| COLNTUT06 | large intestine, cecal tumor, 45 F | 1 | 0.0293 |
| FIBRSEM01 | fibroblasts, senescent, NORM, WM | 1 | 0.0289 |
| LUNGNOT09 | lung, fetal M | 1 | 0.0286 |

FIGURE 10A

| | | | |
|---|---|---|---|
| LUNGNOT12 | lung, 78 M | 1 | 0.0278 |
| THYRNOT03 | thyroid tumor, adenoma, 28 F | 2 | 0.0277 |
| LUNGNOT15 | lung, 69 M, match to LUNGTUT03 | 1 | 0.0276 |
| BRAINOM03 | brain, 55 M, NORM, WM | 1 | 0.0270 |
| PTHYTUM01 | parathyroid tumor, adenoma, M/F, NORM, WM | 1 | 0.0268 |
| PENITUT01 | penis tumor, carcinoma, 64 M | 1 | 0.0267 |
| UTRSNOT08 | uterus, endometrium, 35 F | 1 | 0.0267 |
| BRAITUT13 | brain tumor, meningioma, 68 M | 1 | 0.0262 |
| URETTUT01 | ureter tumor, 69 M | 1 | 0.0262 |
| MPHGNOT03 | macrophages (adher PBMNC), M/F | 2 | 0.0259 |
| BRSTTUT08 | breast tumor, 45 F, match to BRSTNOT09 | 1 | 0.0254 |
| HIPONOT01 | brain, hippocampus, 72 F | 1 | 0.0239 |
| BRSTNOT02 | breast, 55 F, match to BRSTTUT01 | 2 | 0.0222 |
| PANCNOT01 | pancreas, 29 M | 1 | 0.0214 |
| COLNNOT01 | colon, 75 M, match to COLNTUT02 | 1 | 0.0213 |
| TMLR2DT01 | lymphocytes (non-adher PBMNC), M/F, 24-hr MLR | 1 | 0.0212 |
| ENDCNOT03 | endothelial cells, dermal microvascular, neonatal M | 1 | 0.0210 |
| SCORNOT01 | spinal cord, 71 M | 1 | 0.0201 |
| LUNGNOT03 | lung, 79 M, match to LUNGTUT02 | 1 | 0.0200 |
| BRSTTUT03 | breast tumor, 58 F, match to BRSTNOT05 | 2 | 0.0197 |
| CRBLNOT01 | brain, cerebellum, 69 M | 1 | 0.0195 |
| MELANOM01 | melanocytes, M, NORM, WM | 2 | 0.0192 |
| THP1AZT01 | THP-1 promonocyte cell line, treated AZ | 1 | 0.0185 |
| KERANOT02 | keratinocytes, primary cell line, 30 F | 1 | 0.0182 |
| OVARNOT03 | ovary, 43 F, match to OVARTUT01 | 1 | 0.0167 |
| BRAITUT02 | brain tumor, metastasis, 58 M | 2 | 0.0149 |
| BEPINOT01 | bronchial epithelium, primary cell line, 54 M | 1 | 0.0144 |
| BRAITUT01 | brain tumor, oligoastrocytoma, 50 F | 1 | 0.0134 |

FIGURE 10B

| | | | |
|---|---|---|---|
| TESTNOT03 | testis, 37 M | 1 | 0.0129 |
| THP1NOT03 | THP-1 promonocyte cell line, untreated | 1 | 0.0129 |
| ENDANOT01 | endothelial cells, aorta, M | 1 | 0.0128 |
| BLADTUT04 | bladder tumor, 60 M, match to BLADNOT05 | 1 | 0.0127 |
| BRAINON01 | brain, 26 M, NORM | 1 | 0.0099 |
| PANCTUT02 | pancreatic tumor, carcinoma, 45 F | 1 | 0.0086 |
| UCMCL5T01 | mononuclear cells, treated IL-5 | 1 | 0.0084 |
| UTRSNOT02 | uterus, 34 F | 1 | 0.0078 |
| NGANNOT01 | ganglioneuroma, 9 M | 1 | 0.0073 |
| LUNGFET03 | lung, fetal F | 1 | 0.0069 |

FIGURE 10C

| Library | Lib Description | Abun | Pct Abun |
|---|---|---|---|
| ADRENOT01 | adrenal gland, 10-46 M/F | 1 | 0.1052 |
| BRAINOT14 | brain, 40 F, match to BRAITUT12 | 2 | 0.0629 |
| THYRNOT02 | thyroid, hyperthyroidism, 16 F | 2 | 0.0607 |
| SINTNOT13 | small intestine, ileum, ulcerative colitis, 25 F | 2 | 0.0551 |
| LUNGNOT14 | lung, 47 M | 2 | 0.0519 |
| LIVRNOT02 | liver, 32 F | 1 | 0.0517 |
| COLNNOT07 | colon, 60 M | 1 | 0.0409 |
| MYOMNOT01 | uterus, myometrium, 43 F | 1 | 0.0409 |
| COLNTUT03 | colon tumor, 62 M, match to COLNNOT16 | 2 | 0.0392 |
| MUSCNOT02 | muscle, psoas, 12 M | 1 | 0.0386 |
| PLACNOM03 | placenta, fetal, NORM, WM | 1 | 0.0363 |
| BRAINOT04 | brain, choroid plexus, hemorrhage, 44 M | 1 | 0.0356 |
| DUODNOT01 | small intestine, duodenum, 41 F | 1 | 0.0287 |
| LUNGNOT09 | lung, fetal M | 1 | 0.0286 |
| SININOT01 | small intestine, ileum, 4 F | 1 | 0.0280 |
| BLADTUT07 | bladder, microfoci tumor, 58 M | 1 | 0.0278 |
| BEPINON01 | bronchial epithelium, primary cell line, 54 M, NORM | 1 | 0.0274 |
| HYPONOB01 | hypothalamus, 16-75 M/F | 1 | 0.0272 |
| CONNTUT01 | skull tumor, chondroid chordoma, 30 F | 1 | 0.0271 |
| BMARNOT02 | bone marrow, 16-70 M/F | 1 | 0.0270 |
| BRAINOM03 | brain, 55 M, NORM, WM | 1 | 0.0270 |
| KIDNNOT09 | kidney, fetal M | 1 | 0.0267 |
| PROSTUT08 | prostate tumor, 60 M, match to PROSNOT14 | 1 | 0.0266 |
| PROSNOT16 | prostate, 68 M | 2 | 0.0263 |
| LUNGNOT10 | lung, fetal M | 1 | 0.0261 |
| CONUTUT01 | mesentery tumor, sigmoid, 61 F | 2 | 0.0260 |
| TESTNOT03 | testis, 37 M | 2 | 0.0258 |

FIGURE 11A

| | | | |
|---|---|---|---|
| PROSNOT14 | prostate, 60 M, match to PROSTUT08 | 1 | 0.0256 |
| MMLR1DT01 | macrophages (adher PBMNC), M/F, 24-hr MLR | 1 | 0.0236 |
| COLNNOT01 | colon, 75 M, match to COLNTUT02 | 1 | 0.0213 |
| COLNNOT16 | colon, sigmoid, 62 M, match to COLNTUT03 | 1 | 0.0208 |
| CERVNOT01 | cervix, 35 F | 1 | 0.0194 |
| HNT2AGT01 | hNT2 cell line, post-mitotic neurons | 1 | 0.0192 |
| ADENINB01 | adenoid, inflamed, 3y | 1 | 0.0190 |
| HNT2RAT01 | hNT2 cell line, teratocarcinoma, treated RA | 1 | 0.0188 |
| PLACNOT02 | placenta, fetal F | 1 | 0.0168 |
| BRAITUT03 | brain tumor, astrocytoma, 17 F | 1 | 0.0148 |
| BRSTNOT07 | breast, 43 F | 2 | 0.0146 |
| BEPINOT01 | bronchial epithelium, primary cell line, 54 M | 1 | 0.0144 |
| COLNFET02 | colon, fetal F | 1 | 0.0143 |
| LATRTUT02 | heart tumor, myoma, 43 M | 1 | 0.0137 |
| SINTFET03 | small intestine, fetal F | 1 | 0.0130 |
| SPLNFET02 | spleen, fetal M | 1 | 0.0126 |
| PROSTUT04 | prostate tumor, 57 M, match to PROSNOT06 | 1 | 0.0117 |
| OVARNOT02 | ovary, 59 F | 1 | 0.0112 |
| KIDNNOT05 | kidney, neonatal F | 1 | 0.0106 |
| CORPNOT02 | brain, corpus callosum, Alzheimer's, 74 M | 1 | 0.0103 |
| PROSNON01 | prostate, 28 M, NORM | 1 | 0.0094 |
| BRAINOT09 | brain, fetal M | 1 | 0.0093 |
| CARDFEM01 | heart, fetal, NORM, WM | 1 | 0.0083 |
| BRAITUT02 | brain tumor, metastasis, 58 M | 1 | 0.0075 |
| NGANNOT01 | ganglioneuroma, 9 M | 1 | 0.0073 |
| LUNGFET03 | lung, fetal F | 1 | 0.0069 |
| LIVSFEM02 | liver/spleen, fetal M, NORM, WM | 2 | 0.0053 |

FIGURE 11B

| Library | Lib Description | Abun | Pct Abun |
|---|---|---|---|
| BRSTNOM02 | breast, F, NORM, WM | 8 | 0.1652 |
| THP1PLB01 | THP-1 promonocyte cell line, treated PMA, LPS | 3 | 0.1357 |
| COCHFEM01 | ear, cochlea, fetal, WM | 1 | 0.1157 |
| HMC1NOT01 | HMC-1 mast cell line, 52 F | 3 | 0.1003 |
| MMLR3DT01 | macrophages (adher PBMNC), M/F, 72-hr MLR | 3 | 0.0996 |
| PINENOM01 | pineal gland, M/F, NORM, WM | 1 | 0.0890 |
| THP1NOT01 | THP-1 promonocyte cell line, untreated | 1 | 0.0571 |
| MMLR2DT01 | macrophages (adher PBMNC), M/F, 48-hr MLR | 3 | 0.0533 |
| NEUTFMT01 | granulocytes, periph blood, M/F, treated fMLP | 3 | 0.0525 |
| NEUTLPT01 | granulocytes, periph blood, M/F, treated LPS | 3 | 0.0520 |
| MPHGNOT03 | macrophages (adher PBMNC), M/F | 4 | 0.0517 |
| MMLR1DT01 | macrophages (adher PBMNC), M/F, 24-hr MLR | 2 | 0.0472 |
| CARDNOT01 | heart, 65 M | 1 | 0.0404 |
| SINTTUT01 | small intestine tumor, ileum, 42 M | 1 | 0.0382 |
| HUVESTB01 | HUVEC endothelial cell line, shear stress | 1 | 0.0359 |
| PROSTUT03 | prostate tumor, 67 M, match to PROSNOT05 | 1 | 0.0352 |
| SPLNFET01 | spleen, fetal | 1 | 0.0352 |
| LVENNOT03 | heart, left ventricle, 31 M | 1 | 0.0339 |
| BRAINOT11 | brain, right temporal, epilepsy, 5 M | 1 | 0.0322 |
| LUNGNOT18 | lung, 66 F | 1 | 0.0298 |
| DUODNOT01 | small intestine, duodenum, 41 F | 1 | 0.0287 |
| LUNGNOT09 | lung, fetal M | 1 | 0.0286 |
| STOMTUT02 | stomach tumor, lymphoma, 68 F | 1 | 0.0284 |
| LUNGNOT12 | lung, 78 M | 1 | 0.0278 |
| THYRTUT03 | thyroid tumor, benign, 17 M | 1 | 0.0276 |
| LATRTUT02 | heart tumor, myoma, 43 M | 2 | 0.0275 |
| BRAITUT12 | brain tumor, astrocytoma, 49 F, match to BRAINOT14 | 1 | 0.0272 |

FIGURE 12A

| | | | |
|---|---|---|---|
| SEMVNOT01 | seminal vesicle, 58 M | 1 | 0.0272 |
| BLADNOT03 | bladder, 80 F, match to BLADTUT02 | 1 | 0.0271 |
| PTHYTUM01 | parathyroid tumor, adenoma, M/F, NORM, WM | 1 | 0.0268 |
| LUNGNOM01 | lung, 72 M, WM | 1 | 0.0267 |
| LEUKNOT03 | white blood cells, 27 F | 1 | 0.0262 |
| URETTUT01 | ureter tumor, 69 M | 1 | 0.0262 |
| PROSNOT18 | prostate, 58 M | 1 | 0.0256 |
| LIVRNOM01 | liver, 49 M, WM | 1 | 0.0254 |
| TLYMNOT02 | lymphocytes (non-adher PBMNC), M/F | 1 | 0.0254 |
| PANCNOT08 | pancreas, 65 F, match to PANCTUT01 | 1 | 0.0254 |
| SPLNFET02 | spleen, fetal M | 2 | 0.0252 |
| PROSNOT06 | prostate, 57 M, match to PROSTUT04 | 2 | 0.0229 |
| BRAITUT02 | brain tumor, metastasis, 58 M | 3 | 0.0224 |
| BRSTNOT02 | breast, 55 F, match to BRSTTUT01 | 2 | 0.0222 |
| LIVSFEM02 | liver/spleen, fetal M, NORM, WM | 8 | 0.0211 |
| LUNGNOT03 | lung, 79 M, match to LUNGTUT02 | 1 | 0.0200 |
| BRAINON01 | brain, 26 M, NORM | 2 | 0.0197 |
| BRSTTUT03 | breast tumor, 58 F, match to BRSTNOT05 | 2 | 0.0197 |
| ISLTNOT01 | pancreas, islet cells, M/F | 3 | 0.0193 |
| ADENINB01 | adenoid, inflamed, 3y | 1 | 0.0190 |
| PROSNON01 | prostate, 28 M, NORM | 2 | 0.0188 |
| SYNOOAT01 | synovium, knee, osteoarthritis, 82 F | 1 | 0.0180 |
| SYNORAT03 | synovium, wrist, rheumatoid, 56 F | 1 | 0.0170 |
| PANCNOT04 | pancreas, 5 M | 1 | 0.0169 |
| PLACNOT02 | placenta, fetal F | 1 | 0.0168 |
| LUNGTUT03 | lung tumor, 69 M, match to LUNGNOT15 | 1 | 0.0159 |
| PROSTUT05 | prostate tumor, 69 M, match to PROSNOT07 | 1 | 0.0145 |
| TESTTUT02 | testicular tumor, 31 M | 1 | 0.0134 |

FIGURE 12B

| | | | |
|---|---|---|---|
| CONUTUT01 | mesentery tumor, sigmoid, 61 F | 1 | 0.0130 |
| SINTFET03 | small intestine, fetal F | 1 | 0.0130 |
| THP1NOT03 | THP-1 promonocyte cell line, untreated | 1 | 0.0129 |
| EOSIHET02 | eosinophils, hypereosinophilia, 48 M | 1 | 0.0105 |
| BRSTNOT04 | breast, 62 F | 1 | 0.0096 |
| BRAINOT09 | brain, fetal M | 1 | 0.0093 |
| UCMCL5T01 | mononuclear cells, treated IL-5 | 1 | 0.0084 |
| CARDFEM01 | heart, fetal, NORM, WM | 1 | 0.0083 |
| UTRSNOT02 | uterus, 34 F | 1 | 0.0078 |
| BRSTNOT05 | breast, 58 F, match to BRSTTUT03 | 1 | 0.0075 |
| BRAITUT03 | brain tumor, astrocytoma, 17 F | 1 | 0.0074 |
| NGANNOT01 | ganglioneuroma, 9 M | 1 | 0.0073 |
| LUNGFET03 | lung, fetal F | 1 | 0.0069 |
| PLACNOM02 | placenta, neonatal F, NORM, WM | 1 | 0.0056 |

FIGURE 12C

HUMAN ZINC BINDING PROTEINS

FIELD OF THE INVENTION

This invention relates to nucleic acid and amino acid sequences of zinc binding proteins and to the use of these sequences in the diagnosis, prevention, and treatment of diseases related to disregulated cell growth and proliferation including cancer.

BACKGROUND OF THE INVENTION

Zinc binding (ZB) domains are found in numerous proteins which are involved in protein-nucleic acid or protein-protein interactions. ZB proteins are commonly involved in the regulation of gene expression, and may serve as transcription factors and signal transduction molecules. A ZB domain is generally composed of 25 to 30 amino acid residues which form one or more tetrahedral ion binding sites. The binding sites contain four ligands consisting of the sidechains of cysteine, histidine and occasionally aspartate or glutamate. The binding of zinc allows the relatively short stretches of polypeptide to fold into defined structural units which are well-suited to participate in macromolecular interactions (Berg, J. M. et al. (1996) Science 271:1081–1085).

Classes of ZB domains are characterized according to the number and positions of the residues involved in the zinc atom coordination. ZB domains of the $C_2H_2$ type were first identified in the protein transcription factor IIIA (TFIIIA; Hanas, J. et al. (1983) J. Biol. Chem. 258:14120–14125) and represent the most abundant DNA binding motif in eukaryotic transcription factors (Berg, supra). These domains, also known as "zinc fingers", are characterized by tandem arrays of sequences that approximate the consensus sequence (Tyr, Phe)-X-Cys-$X_{(2-4)}$-Cys-$X_3$-Phe-$X_5$-Leu-$X_2$-His-$X_{(3-5)}$-His, wherein X represents a more variable amino acid. The cysteine and histidine residues coordinate a zinc ion, the three other conserved residues form a hydrophobic core adjacent to the metal coordination unit, and the variable amino acids mediate interactions with other molecules. The overall structure consists of two antiparallel β-strands adjacent to an α-helix (Berg, supra). A protein may contain one or more zinc fingers which interact independently of each other. In many instances, proteins which contain zinc finger domains interact with specific double-stranded DNA (dsDNA) sequences, and carry out roles as transcription factors. Some zinc finger proteins, such as TFIIIA, bind to both dsDNA and to single-stranded RNA, while others, such as p43, appear to bind only to single-stranded 5S RNA (Berg, supra). Furthermore, certain zinc finger proteins, including the human transcription factor SP1, bind DNA-RNA heteroduplexes with affinities comparable to or greater than those for DNA duplexes (Shi, Y. et al. (1995) Science 268:282–284).

A variant of the zinc finger described by a $C_2C_2$ sequence motif is found in the Xenopus G10 protein (McGrew, L. L. et al. (1989) Genes Dev. 3: 803–815). G10 mRNA is a maternal transcript that is translationally activated during oocyte maturation. G10 protein consists of N-terminal containing a nuclear translocation signal (NTS) and alternating acidic and basic residues, and C-terminal sequence containing the $C_2C_2$ -type zinc finger motif. G10 appears to function as a nuclear regulatory protein (McGrew et al., supra). Sequences highly homologous to G10 have been found in various organisms, including C. elegans, rice, and S. cerevisiae (Benit, P. et al. (1992) Yeast 8:147–153).

ZB domains which contain a $C_3HC_4$ sequence motif are known as RING domains (Lovering, R. et al. (1993) Proc. Natl. Acad. Sci. USA 90:2112–2116). The RING domain binds two zinc ions in an arrangement structurally different from that of the zinc finger. The RING domain consists of eight metal binding residues, and the sequences that bind the two metal ions overlap (Barlow, P. N. et al. (1994) J. Mol. Biol. 237:201–211). The consensus sequence $C-X_2-C-X_{(9-27)}-C-X_{(1-3)}-H-X_{(2-3)}-C-X_2-C-X_{(4-48)}-C-X_2-C$ provides for loops of varying length which form the overlapping Zn binding sites. The two Zn binding sites are formed by four pairs of metal-binding Cys and His residues. The first and third pairs bind one metal ion, while the second and fourth pairs bind the other (Barlow, et al., supra). Functions of RING finger proteins are mediated through DNA binding and include the regulation of gene expression, DNA recombination, and DNA repair.

The murine BMI-1 gene encodes a protein of 324 amino acids. This protein, which is found in the nuclei of a variety of normal cells, contains a RING domain near the amino-terminus (Haupt, Y. et al. (1991) Cell 65:753–763). Retroviral insertional mutagenesis of E-mu/myc transgenic mice by infection with Moloney murine leukemia virus (MuLV) accelerates development of B lymphoid tumors. In about half of independently induced pre-B-cell lymphomas, the provirus integrates in or near the BMI-1 gene, which results in enhanced transcription of that gene. Haupt et al. (supra) concluded that myc-induced lymphomagenesis may entail the concerted action of several genes, including the putative nuclear regulator BMI-1. The human BMI-1 gene encodes a protein of 326 amino acids which shares 98% identity to the amino acid sequence of the mouse protein (Alkema, M. J. et al. (1993) Hum. Mol. Genet. 2:1597–1603). Fluorescence in situ hybridization (FISH) on metaphase chromosome spreads localized the human BMI-1 proto-oncogene to the short arm of chromosome 10 (10p13), a region known to be involved in translocations in various leukemias (Alkema et al., supra).

The breast and ovarian cancer susceptibility-1 (BRCA1) gene encodes a predicted protein of 1,863 amino acids which contains a RING domain in the amino-terminal region (Miki, Y. et al. (1994) Science 266:66–71). BRCA1 is expressed in numerous tissues, including breast and ovary. In sporadic breast cancer, BRCA1 mRNA levels are markedly decreased during the transition from carcinoma in situ to invasive cancer (Thompson M. E. et al. (1995) Nature Genet. 9:444–450). Furthermore, experimental inhibition of BRCA1 expression with antisense oligonucleotides produced accelerated growth of normal and malignant mammary cells, but had no effect on nonmammary epithelial cells. Thompson et al. interpreted these results as an indication that BRCA1 may normally serve as a negative regulator of mammary epithelial cell growth and that this function is compromised in breast cancer either by direct mutation or by alterations in gene expression.

A variation of the RING finger motif in which a His replaces the fourth Cys of the consensus ($C_3HHC_3$) is found in the protein product of the Drosophila developmental gene goliath (G1; Bouchard M. L. et al. (1993) Gene 125:205–209). The G1 gene is an abundant transcript of the visceral mesoderm of the Drosophila embryo. Mesoderm is one of the fundamental embryonic germ layers which gives rise to internal structures such as the body and gut musculature, fat body and heart. A high frequency of hydrophobic and uncharged residues, primarily Ser, Gln and Pro (SQP-rich region), is found in the last one-third of the G1 protein. Based on the observation that similar domains impart transcriptional activation ability to eukaryotic DNA-binding proteins (Mitchell, P. J. et al. (1989) Science 245:371–378), Bouchard et al. suggest that the SQP-rich region of G1 is a potential transcriptional activation domain.

The discovery of polynucleotides encoding human zinc binding proteins, and the molecules themselves, provides a means to investigate physiological processes relating to the control of cellular differentiation and proliferation under normal and disease conditions. Discovery of novel zinc binding proteins satisfies a need in the art by providing new diagnostic or therapeutic compositions useful in diagnosing and treating diseases relating to disregulated cell growth and proliferation including cancer.

SUMMARY OF THE INVENTION

The present invention features three zinc binding proteins, designated individually as ZB-1, ZB-2 and ZB-3 and collectively as ZB, and characterized as having similarity to the zinc finger protein G10 and the RING domain proteins BMI-1 and G1.

Accordingly, the invention features substantially purified ZB proteins ZB-1, ZB-2, and ZB-3 having the amino acid sequences shown in SEQ ID NO:1, SEQ ID NO:3, and SEQ ID NO:5, respectively.

One aspect of the invention features isolated and substantially purified polynucleotides that encode ZB proteins ZB-1, ZB-2, and ZB-3. In a particular aspect, the polynucleotides are the nucleotide sequences of SEQ ID NO:2, SEQ ID NO:4, or SEQ ID NO:6, respectively.

The invention also features a polynucleotide sequence comprising the complement of SEQ ID NO:2, SEQ ID NO:4, SEQ ID NO:6, or variants thereof. In addition, the invention features polynucleotide sequences which hybridize under stringent conditions to SEQ ID NO:2, SEQ ID NO:4, or SEQ ID NO:6.

The invention additionally features nucleic acid sequences encoding polypeptides, oligonucleotides, peptide nucleic acids (PNA), fragments, portions or antisense molecules thereof, and expression vectors and host cells comprising polynucleotides that encode ZB. The present invention also features antibodies which bind specifically to ZB, and pharmaceutical compositions comprising substantially purified ZB. The invention also features the use of agonists and antagonists of ZB.

BRIEF DESCRIPTION OF THE FIGURES

FIGS. 1A and 1B show the amino acid sequence (SEQ ID NO:1) and nucleic acid sequence (SEQ ID NO:2) of ZB-1. The alignment was produced using MACDNASIS PRO software (Hitachi Software Engineering Co., Ltd., San Bruno, Calif.).

FIG. 2A, 2B and 2C show the amino acid sequence (SEQ ID NO:3) and nucleic acid sequence (SEQ ID NO:4) of ZB-2.

FIGS. 3A, 3B and 3C show the amino acid sequence (SEQ ID NO:5) and nucleic acid sequence (SEQ ID NO:6) of ZB-3.

FIG. 4 shows the amino acid sequence alignment between ZB-1 (SEQ ID NO:1) and G10 protein from *Xenopus laevis* (GI 120625; SEQ ID NO:7). The alignment was produced using the multisequence alignment program of DNASTAR™ software (DNASTAR Inc, Madison Wis.).

FIG. 5 shows the amino acid sequence alignment between ZB-2 (SEQ ID NO:3) and human BMI-1 (GI 461632; SEQ ID NO:8).

FIG. 6 shows the amino acid sequence alignment between ZB-3 (SEQ ID NO:5) and Drosophila G1 protein (GI 157535; SEQ ID NO:9).

FIGS. 10A, 10B and 10C show the northern analysis for SEQ ID NO:2. The northern analysis was produced electronically using LIFESEQ™ database (Incyte Pharmaceuticals, Inc. Palo Alto, Calif.).

FIGS. 11A and 11B shows the northern analysis for SEQ ID NO:4.

FIGS. 12A, 12B and 12C show the northern analysis for SEQ ID NO:6.

DESCRIPTION OF THE INVENTION

Figure 7A:
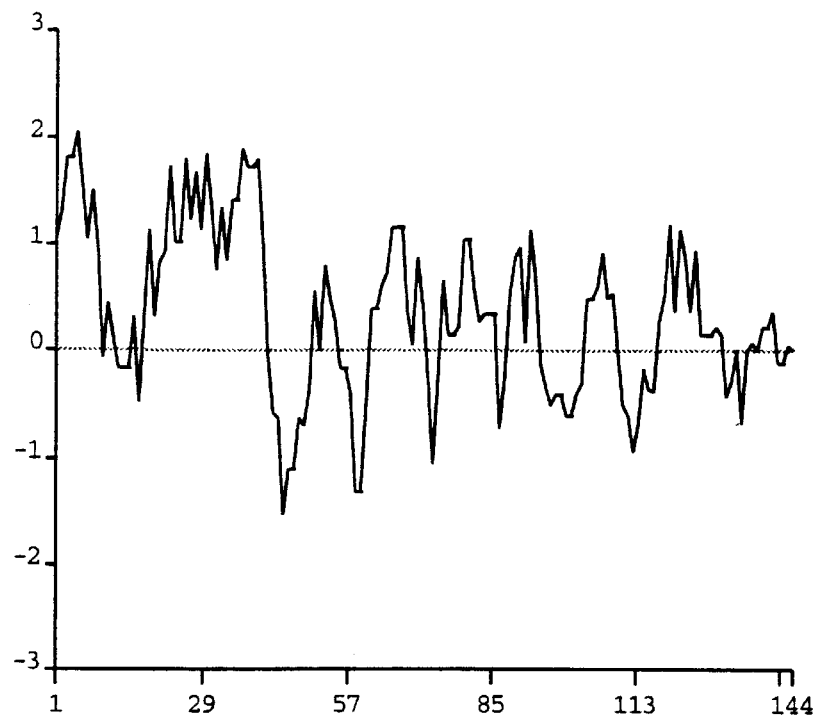
FIGS. 7A and 7B show the hydrophobicity plots (MACDNASIS PRO software) for ZB-1, SEQ ID NO:1 and G10 protein, SEQ ID NO:7; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence", as used herein, refers to an oligonucleotide, nucleotide, or polynucleotide, and fragments or portions thereof, and to DNA or RNA of genomic or synthetic origin which may be single- or double-stranded and represent the sense or antisense strand. Similarly, "amino acid sequence", as used herein, refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

ZB, as used herein, refers to the amino acid sequences of substantially purified ZB obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW fragment assembly system (GCG, Madison, Wis.), or which has been both extended and assembled.

A "variant" of ZB, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic ZB, or any oligopeptide thereof, to induce a specific immune response in appropriate animals or cells and to bind with specific antibodies.

The term "agonist", as used herein, refers to a molecule which, when bound to ZB, causes a change in ZB which modulates the activity of ZB. Agonists may include proteins, nucleic acids, carbohydrates, or any other molecules which bind to ZB.

The terms "antagonist" or "inhibitor", as used herein, refer to a molecule which, when bound to ZB, blocks or modulates the biological or immunological activity of ZB. Antagonists and inhibitors may include proteins, nucleic acids, carbohydrates, or any other molecules which bind to ZB.

The term "modulate", as used herein, refers to a change or an alteration in the biological activity of ZB. Modulation may be an increase or a decrease in protein activity, a change in binding characteristics, or any other change in the biological, functional or immunological properties of ZB.

The term "mimetic", as used herein, refers to a molecule, the structure of which is developed from knowledge of the structure of ZB or portions thereof and, as such, is able to effect some or all of the actions of zinc binding protein-like molecules.

The term "derivative", as used herein, refers to the chemical modification of a nucleic acid encoding ZB or the encoded ZB. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human ZB-1 and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding ZB or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding ZB in a sample and thereby correlates with expression of the transcript from the polynucleotide encoding the protein.

"Alterations" in the polynucleotide of SEQ ID NO:2, SEQ ID NO:4, or SEQ ID NO:6, as used herein, comprise any alteration in the sequence of polynucleotides encoding ZB including deletions, insertions, and point mutations that may be detected using hybridization assays. Included within this definition is the detection of alterations to the genomic DNA sequence which encodes ZB (e.g., by alterations in the pattern of restriction fragment length polymorphisms capable of hybridizing to SEQ ID NO:2, SEQ ID NO:4, or SEQ ID NO:6), the inability of a selected fragment of SEQ ID NO:2, SEQ ID NO:4, or SEQ ID NO:6 to hybridize to a sample of genomic DNA (e.g., using allele-specific oligonucleotide probes), and improper or unexpected hybridization, such as hybridization to a locus other than the normal chromosomal locus for the polynucleotide sequence encoding ZB (e.g., using fluorescent in situ hybridization (FISH) to metaphase chromosome spreads).

As used herein, the term "antibody" refers to intact molecules as well as fragments thereof, such as Fa, F(ab')$_2$, and Fv, which are capable of binding the epitopic determinant. Antibodies that bind ZB polypeptides can be prepared using intact polypeptides or fragments containing small peptides of interest as the immunizing antigen. The polypeptide or peptide used to immunize an animal can be derived from the translation of mRNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of novel human zinc binding proteins (ZB-1, ZB-2, and ZB-3, collectively referred to as ZB), the polynucleotides encoding ZB, and the use of these compositions for the diagnosis, prevention, or treatment of diseases related to disregulated cell growth and proliferation including cancer.

Nucleic acids encoding the human ZB-1 of the present invention were first identified in Incyte Clone 3407, from a human leukemia-derived mast cell line cDNA library (HMC1NOT01) through a computer-generated search for amino acid sequence alignments. A consensus sequence, SEQ ID NO:2, was derived from the following overlapping and/or extended nucleic acid sequences:Incyte Clones 3407 and 3664 (HMC1NOT01); 240102 (HIPONOT01); 863306 (BRAITUT03); 913472 (STOMNOT02); and 1232134 (LUNGFET03).

Nucleic acids encoding the human ZB-2 of the present invention were first identified in Incyte Clone 134194 from a bone marrow cDNA library (BMARNOT02) through a computer-generated search for amino acid sequence alignments. A consensus sequence, SEQ ID NO:4, was derived from the following overlapping and/or extended nucleic acid sequences:Incyte Clones 1298467 (BRSTNOT07); 134194 (BMARNOT02); 280390 (LIVRNOT02); and 879714 (THYRNOT02).

Nucleic acids encoding the human ZB-3 of the present invention were first identified in Incyte Clone 10773 from a human promonocyte THP-1 cell line cDNA library (THP1PLB01) through a computer-generated search for amino acid sequence alignments. A consensus sequence, SEQ ID NO:6, was derived from the following overlapping and/or extended nucleic acid sequences:Incyte Clones 010773 (THP1PLB01); 159486 (ADENINB01); 477520 and 520960 (MMLR2DT01); 562318 (NEUTLPT01); 568606 (MMLR3DT01); and 741106 (PANCNOT04).

Figure 7B:
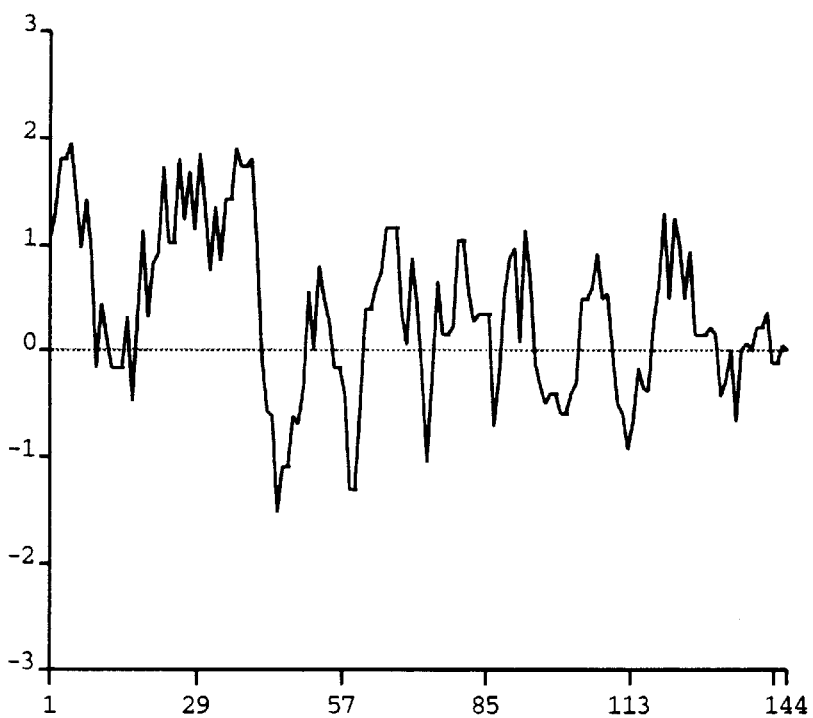

In one embodiment, the invention encompasses a polypeptide comprising the amino acid sequence of SEQ ID NO:1, and shown in FIGS. 1A and 1B. ZB-1 is 144 amino acids in length and contains a potential nuclear translocation signal, consisting of predominantly basic residues extending from position $K_1$ through $K_9$, followed by a region containing a high proportion of acidic residues from $D_{13}$ to $E_{38}$. As shown in FIG. 4, ZB-1 has chemical and structural homology with G10 protein from *Xenopus laevis* (GI 120625; SEQ ID NO:7). In particular, ZB-1 shares 96% amino acid sequence identity with Xenopus G10 protein, and the two proteins have similar hydrophobicity profiles (FIGS. 7A and 7B). The C-terminus of ZB-1 contains a $C_2C_2$-type zinc finger domain spanning positions $C_{101}$ to $C_{119}$. The presence in ZB-1 of a nuclear translation signal and the zinc finger motif suggest a regulatory role in nuclear function. From the northern analysis (FIGS. 10A, 10B and 10C), ZB-1 is expressed in a variety of cell and tissue libraries. Of particular note is the high abundance of ZB-1 in hematopoietic tissues and cells involved in the immune response and its presence in tumor-associated tissues and immortalized cell lines. In addition, ZB-1 is found in several fetal tissue libraries and appears to have a role in fetal development.

Figure 8A:
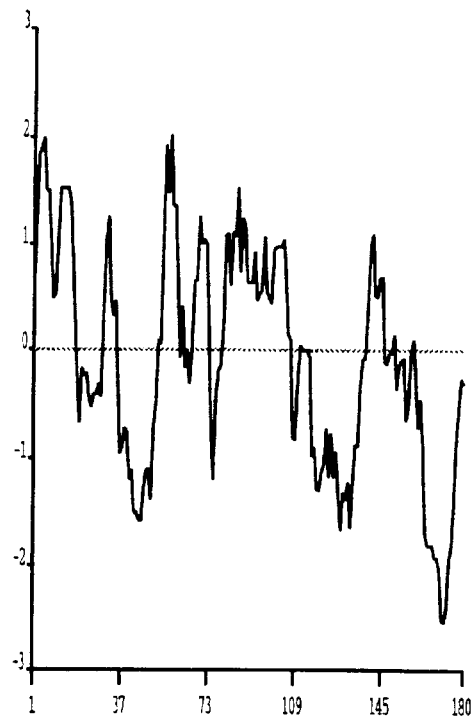
FIGS. 8A and 8B show the hydrophobicity plots for ZB-2, SEQ ID NO:3, and human BMI-1, SEQ ID NO:8.
Figure 8B:
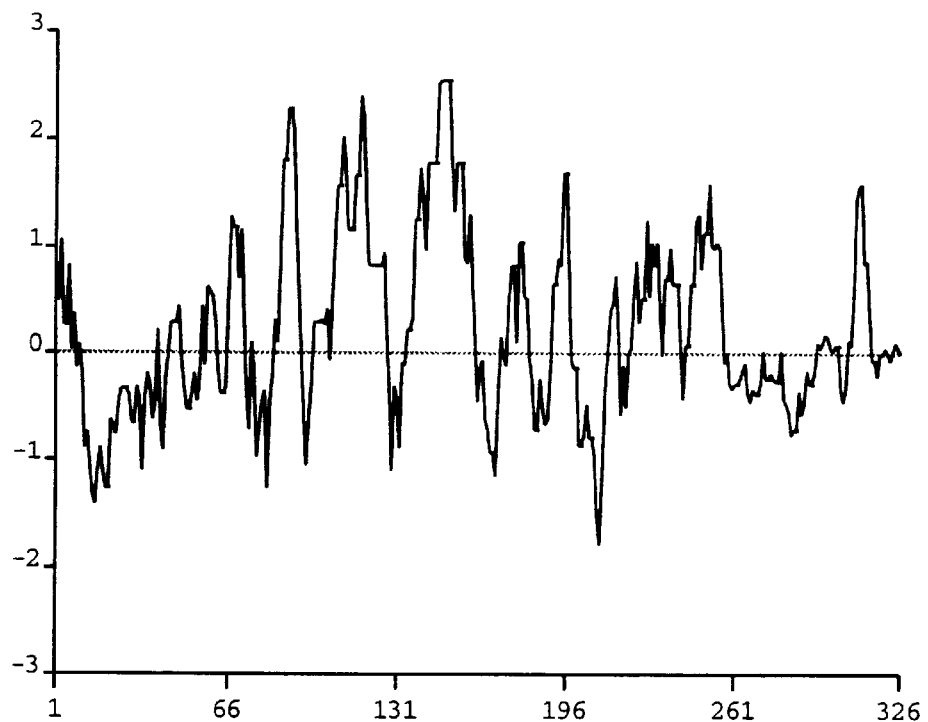

In another embodiment, the invention encompasses the novel zinc binding protein ZB-2, a polypeptide comprising the amino acid sequence of SEQ ID NO:3, as shown in FIGS. 2A, 2B and 2C. ZB-2 is 180 amino acids in length. As shown in FIG. 5, ZB-2 has chemical and structural homology with human BMI-1 (GI 461632; SEQ ID NO:8). In particular, ZB-2 and BMI-1 share 88% identity, and, as illustrated by FIGS. 8A and 8B, have rather similar hydrophobicity plots. ZB-2 contains a single RING domain, defined by amino acids $C_{27}$, $C_{30}$, $C_{42}$, $H_{44}$, $C_{47}$, $C_{50}$, $C_{64}$ and $C_{67}$, which is precisely conserved among proteins involved in gene regulation and oncogenesis including BMI-1. Northern analysis (FIG. 11) reveals the expression of ZB-2 sequence in approximately 50 cDNA libraries prepared from a wide variety of tissues, with highest abundance in adrenal gland, brain, thyroid, small intestine, lung, liver, prostate, colon, uterus, bladder, and bone marrow. Of particular note is the high abundance of ZB-2 in tissues relating to secretion or absorption, and its presence in tumor-associated tissues and immortalized cell lines. In addition, ZB-2 is found in a variety of fetal tissues and appears to have a role in fetal development.

Figure 9A:
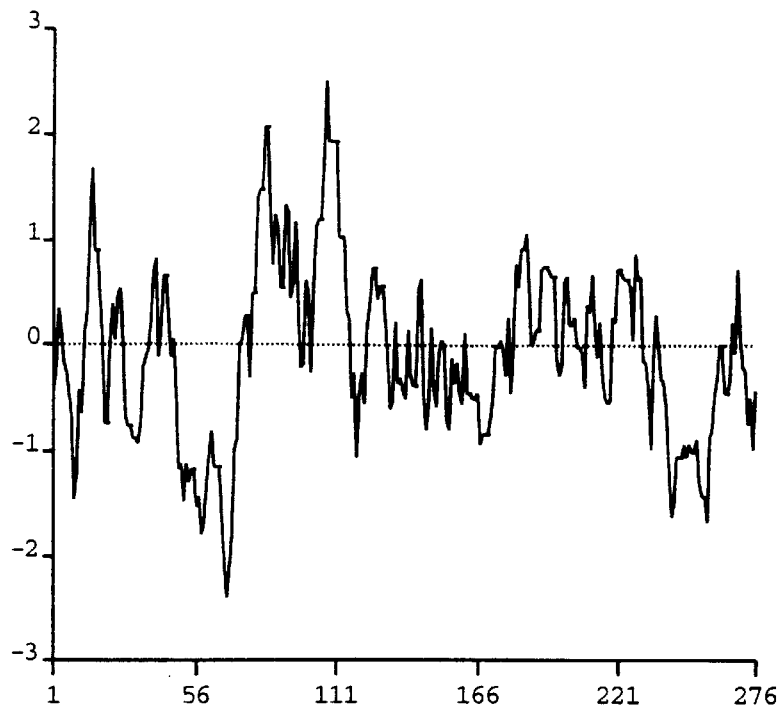
FIGS. 9A and 9B show the hydrophobicity plot for ZB-3, SEQ ID NO:5, and G1 protein, SEQ ID NO:9.
Figure 9B:
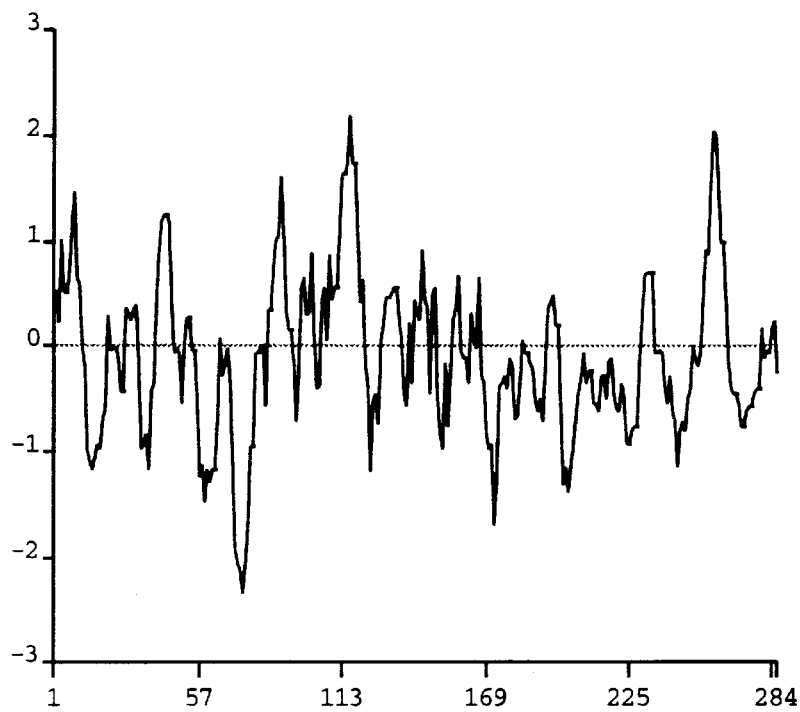

In an additional embodiment, the invention encompasses the novel zinc binding protein ZB-3, a polypeptide comprising the amino acid sequence of SEQ ID NO:5, as shown in FIGS. 3A and 3B. ZB-3 is 276 amino acids in length. As shown in FIG. 6, ZB-3 has chemical and structural homology with Drosophila G1 protein (GI 157535; SEQ ID NO:9). In particular, ZB-3 and G1 share 34% amino acid sequence identity, with maximal identity in their N-terminal sequences. As illustrated by FIGS. 9A and 9B, ZB-3 and G1 have rather similar hydrophobicity plots. The single RING-like domain of ZB-3, defined by amino acids $C_{121}$, $C_{124}$, $C_{139}$, $H_{141}$, $H_{144}$, $C_{147}$, $C_{158}$, and $C_{161}$, is precisely conserved in G1. Northern analysis (FIGS. 12A and 12B) shows the abundant expression of this sequence in hematopoietic cells involved in immune response, including leukemia-derived promonocyte and mast cell lines, macrophages, and granulocytes. ZB-3 encoding sequences are also expressed in glands and organs involved in secretion and absorption, including breast, pineal gland, prostate, stomach, small intestine, bladder, liver, pancreas, and lung. Of particular note is the presence of ZB3 in tumor-associated tissues and immortalized cell lines. In addition, ZB-3 is found in a variety of fetal tissues and appears to have a role in fetal development.

The invention also encompasses ZB variants. A preferred ZB variant is one having at least 80%, and more preferably 90%, amino acid sequence similarity to the ZB amino acid sequence (SEQ ID NO:1, SEQ ID NO:3, or SEQ ID NO:5). A most preferred ZB variant is one having at least 95% amino acid sequence similarity to SEQ ID NO:1, SEQ ID NO:3, or SEQ ID NO:5.

The invention also encompasses polynucleotides which encode ZB. Accordingly, any nucleic acid sequence which encodes the amino acid sequence of ZB can be used to generate recombinant molecules which express ZB. In a particular embodiment, the invention encompasses the polynucleotide comprising the nucleic acid of SEQ ID NO:2, SEQ ID NO:4, or SEQ ID NO:6 as shown in FIGS. 1A, 1B, 2A, 2B, 2C, 3A, 3B and 3C.

It will be appreciated by those skilled in the art that as a result of the degeneracy of the genetic code, a multitude of nucleotide sequences encoding ZB, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ZB, and all such variations are to be considered as being specifically disclosed.

Although nucleotide sequences which encode ZB and its variants are preferably capable of hybridizing to the nucleotide sequence of the naturally occurring ZB under appropriately selected conditions of stringency, it may be advantageous to produce nucleotide sequences encoding ZB or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ZB and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode ZB and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding ZB or any portion thereof.

Also encompassed by the invention are polynucleotide sequences that are capable of hybridizing to the claimed nucleotide sequences, and in particular, those shown in SEQ ID NO:2, SEQ ID NO:4, or SEQ ID NO:6, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–11), and may be used at a defined stringency.

Altered nucleic acid sequences encoding ZB which are encompassed by the invention include deletions, insertions, or substitutions of different nucleotides resulting in a polynucleotide that encodes the same or a functionally equivalent ZB. The encoded protein may also contain deletions, insertions, or substitutions of amino acid residues which produce a silent change and result in a functionally equivalent ZB. Deliberate amino acid substitutions may be made on the basis of similarity in polarity, charge, solubility, hydrophobicity, hydrophilicity, and/or the amphipathic nature of the residues as long as the biological activity of ZB is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding ZB. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE Polymerase (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE amplification system marketed by Gibco BRL (Gaithersburg, Md.). Preferably, the process is automated with machines such as the Hamilton MICRO LAB 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding ZB may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic.2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode ZB, or fusion proteins or functional equivalents thereof, may be used in recombinant DNA molecules to direct expression of ZB in appropriate host cells. Due to the inherent degeneracy of the genetic code, other DNA sequences which encode substantially the same or a functionally equivalent amino acid sequence may be produced and these sequences may be used to clone and express ZB.

As will be understood by those of skill in the art, it may be advantageous to produce ZB-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter sequences encoding ZB for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, to alter glycosylation patterns, to change codon preference, to produce splice variants, or to introduce mutations, and so forth.

In another embodiment of the invention, natural, modified, or recombinant polynucleotides encoding ZB may be ligated to a heterologous sequence to encode a fusion protein. For example, to screen peptide libraries for inhibitors of ZB activity, it may be useful to encode a chimeric ZB protein that can be recognized by a commercially available antibody. A fusion protein may also be engineered to contain a cleavage site located between a sequence encoding ZB and the heterologous protein sequence, so that ZB may be cleaved and purified away from the heterologous moiety.

In another embodiment, sequences encoding ZB may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of ZB, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of ZB, or any part thereof, may be altered during direct synthesis and/or combined using chemical methods with sequences from other proteins, or any part thereof, to produce a variant polypeptide.

In order to express a biologically active ZB, the nucleotide sequences encoding ZB or functional equivalents, may be inserted into appropriate expression vectors, i.e., a vector which contains the necessary elements for the transcription and translation of the inserted coding sequence.

Methods which are well known to those skilled in the art may be used to construct expression vectors containing sequences encoding ZB and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding ZB. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL), and the like, may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ZB, vectors based on SV40 or EBV may be used with an appropriate selectable marker.

In bacterial systems, a number of expression vectors may be selected depending upon the use intended for ZB. For example, when large quantities of ZB are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding ZB may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding ZB may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express ZB. For example, in one such system, *Autographa californica* nuclear polyhedrosis virus (AcNPV) is used as a vector to express foreign genes in *Spodoptera frugiperda* cells or in Trichoplusia larvae. The sequences encoding ZB may be cloned into a non-essential region of the virus, such as the polyhedrin gene, and placed under control of the polyhedrin promoter. Successful insertion of ZB will render the polyhedrin gene inactive and produce recombinant virus lacking coat protein. The recombinant viruses may then be used to infect, for example, *S. grugiperda* cells or Trichoplusia larvae in which ZB may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding ZB may be ligated into an adenovirus transcription/translation complex consisting of the late promoter and tripartite leader sequence. Insertion in a non-essential E1 or E3 region of the viral genome may be used to obtain a viable virus which is capable of expressing ZB in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding ZB. Such signals include the ATG initiation codon and adjacent sequences. In cases where sequences encoding ZB, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express ZB may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra).

Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding ZB is inserted within a marker gene sequence, recombinant cells containing sequences encoding ZB can be identified by the absence of marker gene function. Alternatively, a marker gene can be placed in tandem with a sequence encoding ZB under the control of a single promoter. Expression of the marker gene in response to induction or selection usually indicates expression of the tandem gene as well.

Alternatively, host cells which contain sequences encoding and expressing ZB may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of the nucleic acid or protein.

The presence of polynucleotide sequences encoding ZB can be detected by DNA—DNA or DNA-RNA hybridization or amplification using probes or portions or fragments of polynucleotides encoding ZB. Nucleic acid amplification based assays involve the use of oligonucleotides or oligomers based on the sequences encoding ZB to detect transformants containing DNA or RNA encoding ZB. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of ZB, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ZB is preferred, but a competitive binding assay may be employed. These and other assays are described, among other places, in Hampton, R. et al. (1990*; Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ZB include oligolabeling, nick translation, end-labeling or PCR amplification using a labeled nucleotide. Alternatively, sequences encoding ZB, or any portion thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits from Pharmacia & Upjohn (Kalamazoo, Mich.); Promega (Madison, Wis.); and U.S. Biochemical Corp. (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding ZB may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode ZB may be designed to contain signal sequences which direct secretion of ZB through a prokaryotic or eukaryotic cell membrane. Other recombinant constructions may be used to join sequences encoding ZB to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ZB may be used to facilitate purification. One such expression vector provides for expression of a fusion protein containing ZB and a nucleic acid encoding 6 histidine residues preceding a thioredoxin or an enterokinase cleavage site. The histidine residues facilitate purification on IMIAC (immobilized metal ion affinity chromatography) as described in Porath, J. et al. (1992, Prot. Exp. Purif. 3:263–281) while the enterokinase cleavage site provides a means for purifying ZB from the fusion protein. A discussion of vectors which contain fusion proteins is provided in Kroll, D. J. et al. (1993; DNA Cell Biol. 12:441–453).

In addition to recombinant production, fragments of ZB may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of ZB may be chemically synthesized separately and combined using chemical methods to produce the full length molecule.

THERAPEUTICS

Based on the chemical and structural homology between ZB-1 and Xenopus G10, ZB-2 and human BMI-1, and ZB-3 and Drosophila G1, ZB appears to play a role in cellular development and differentiation and may be involved in disorders relating to abnormal cell differentiation and proliferation including cancer. ZB is expressed in hematopoietic cells, brain, neuronal, and epithelial tissues, glands and tissues relating to secretion or absorption, developing fetal tissues, and tissues associated with tumors and immortalized cell lines.

Therefore, in one embodiment, ZB or a fragment or derivative thereof may be used to treat cells in vivo or ex vivo for the purposes of tissue or organ regeneration. This embodiment would be of particular benefit in the proliferation and differentiation of hematopoietic, nerve, epithelial or secretory cells.

In another embodiment, a vector capable of expressing ZB, or a fragment or derivative thereof, may also be administered to a cell culture or a subject for ex vivo or in vivo therapy as described above.

In another embodiment, a vector expressing antisense of the polynucleotide encoding ZB may be administered to a subject to treat or prevent disorders which are associated with expression of ZB. Such disorders may include, but are not limited to, cancers of hematopoietic cells and tissues including leukemias, lymphomas, lymphosarcomas and myelomas; cancers of brain and neuronal tissues including neuromas, neurogliomas, meningiomas, neuroblastomas and astrocytomas; cancers of glands, tissues, and organs involved in secretion or absorption, including adrenal gland, thyroid, lung, pancreas, liver, prostate, uterus, bladder, kidney, testes, and the gastrointestinal tract (small intestine, colon, rectum, and stomach); and other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease.

In another embodiment, antagonists or inhibitors of ZB may be administered to a subject to treat or prevent any of the diseases or disorders described above. In a particular aspect, antibodies which are specific for ZB may be used directly as an antagonist, or indirectly as a targeting or delivery mechanism for bringing a pharmaceutical agent to cells or tissues which express ZB.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of ZB may be produced using methods which are generally known in the art. In particular, purified ZB may be used to produce antibodies or to screen libraries of pharmaceutical agents to identify those which specifically bind ZB.

Antibodies which are specific for ZB may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ZB or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to ZB have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of ZB amino acids may be fused with those of another protein such as keyhole limpet hemocyanin and antibody produced against the chimeric molecule.

Monoclonal antibodies to ZB may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J Immunol. Methods 81:31–42; Cote, R. J. et al. (1983) Proc. Natl. Acad. Sci. 80:2026–2030; Cole, S. P. et al. (1985) Mol Cell Biol. 62:109–120.

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–55; Neuberger, M. S. et al. (1984) Nature 312:604–8; Takeda, S. et al. (1985) Nature 314:452–4). Alternatively, techniques described for the production of single chain antibodies may be adapted, using methods known in the art, to produce ZB-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–37; Winter, G. et al. (1991) Nature 349:293–9).

Antibody fragments which contain specific binding sites for ZB may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–81).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ZB and its specific antibody. A two-site, monoclonal-based immunoassay utilizing monoclonal antibodies reactive to two non-interfering ZB epitopes is preferred, but a competitive binding assay may also be employed (Maddox, supra).

In another embodiment of the invention, the polynucleotides encoding ZB, or any fragment thereof, or antisense molecules, may be used for therapeutic purposes. In one aspect, antisense to the polynucleotide encoding ZB may be used in situations in which it would be desirable to block the transcription of mRNA. In particular, cells may be transformed with sequences complementary to polynucleotides encoding ZB. Thus, antisense sequences may be used to modulate ZB activity, or to achieve regulation of gene function. Such technology is now well known in the art, and sense or antisense oligomers or larger fragments, can be designed from various locations along the coding or control regions of sequences encoding ZB.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding ZB. These techniques are described both in Sambrook et al. (supra) and in Ausubel et al. (supra).

Genes encoding native ZB can be turned off by transforming a cell or tissue with expression vectors which express high levels of the polynucleotide, or fragment thereof, which encodes ZB. Such constructs may be used to introduce untranslatable sense or antisense sequences into a cell. Even in the absence of integration into the genomic DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding ZB, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ZB.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding ZB. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ZB, antibodies to ZB, mimetics, agonists, antagonists, or inhibitors of ZB. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffer saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ZB, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example ZB or fragments thereof, antibodies of ZB, agonists, antagonists or inhibitors of ZB, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind ZB may be used for the diagnosis of conditions or diseases characterized by expression of ZB, or in assays to monitor patients being treated with ZB, agonists, antagonists or inhibitors. The antibodies useful for diagnostic purposes may be prepared in the same manner as those described above for therapeutics. Diagnostic assays for ZB include methods which utilize the antibody and a label to detect ZB in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ZB are known in the art and provide a basis for diagnosing altered or abnormal levels of ZB expression. Normal or standard values for ZB expression are established by combining body fluids or cell extracts taken from normal mammalian subjects, preferably human, with antibody to ZB under conditions suitable for complex formation. The amount of standard complex formation may be quantified by various methods, but preferably by photometric means. Quantities of ZB expressed in subject samples, control and disease from biopsied tissues are compared with the standard values. Deviation between standard and subject values establishes the parameters for diagnosing disease.

In another embodiment of the invention, the polynucleotides encoding ZB may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of ZB may be correlated with disease. The diagnostic assay may be used to distinguish between absence, presence, and excess expression of ZB, and to monitor regulation of ZB levels during therapeutic intervention.

In one aspect, hybridization with PCR probes which are capable of detecting polynucleotide sequences, including genomic sequences, encoding ZB or closely related molecules, may be used to identify nucleic acid sequences which encode ZB. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding ZB, alleles, or related sequences.

Probes may also be used for the detection of related sequences, and should preferably contain at least 50% of the nucleotides from any of the sequences encoding ZB. The hybridization probes of the subject invention may be DNA or RNA and derived from the nucleotide sequences of SEQ ID NO:2, SEQ ID NO:4, or SEQ ID NO:6 or from genomic sequence including promoter, enhancer elements, and introns of the naturally occurring ZB.

Means for producing specific hybridization probes for DNAs encoding ZB include the cloning of nucleic acid sequences encoding ZB or ZB derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding ZB may be used for the diagnosis of disorders which are associated with expression of ZB. Examples of such disorders include cancers of hematopoietic cells and tissues including leukemias, lymphomas, lymphosarcomas and myelomas; cancers of brain and neuronal tissues including neuromas, neurogliomas, meningiomas, neuroblastomas and astrocytomas; cancers of glands, tissues, and organs involved in secretion or absorption, including adrenal gland, thyroid, lung, pancreas, liver, prostate, uterus, bladder, kidney, and testes, and organs of the gastrointestinal tract including small intestine, colon, rectum, and stomach; other disorders relating to abnormal cellular differentiation, proliferation, or degeneration, including hyperaldosteronism, hypocortisolism (Addison's disease), hyperthyroidism (Grave's disease), hypothyroidism, colorectal polyps, gastritis, gastric and duodenal ulcers, ulcerative colitis, and Crohn's disease. The polynucleotide sequences encoding ZB may be used in Southern or northern analysis, dot blot, or other membrane-based technologies; in PCR technologies; or in dip stick, pin, ELISA or chip assays utilizing fluids or tissues from patient biopsies to detect altered ZB expression. Such qualitative or quantitative methods are well known in the art.

In a particular aspect, the nucleotide sequences encoding ZB may be useful in assays that detect activation or induction of various cancers, particularly those mentioned above. The nucleotide sequences encoding ZB may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding ZB in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ZB, a normal or standard profile for expression is established. This may be accomplished by combining body fluids or cell extracts taken from normal subjects, either animal or human, with a sequence, or a fragment thereof, which encodes ZB, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively low amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding ZB may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of ZB include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes ZB may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma, R. S. et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding ZB on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, ZB, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ZB and the agent being tested, may be measured.

Another technique for drug screening which may be used provides for high throughput screening of compounds having suitable binding affinity to the protein of interest as described in published PCT application WO84/03564. In this method, as applied to ZB, large numbers of different small test compounds are synthesized on a solid substrate, such as plastic pins or some other surface. The test compounds are reacted with ZB, or fragments thereof, and washed. Bound ZB is then detected by methods well known in the art. Purified ZB can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding ZB specifically compete with a test compound for binding ZB. In this manner, the antibodies can be used to detect the presence of any peptide which shares one or more antigenic determinants with ZB.

In additional embodiments, the nucleotide sequences which encode ZB may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

HMC1NOT01

The human mast cell HMCNOTO1 cDNA library was constructed by Stratagene using mRNA purified from cultured HMC-1 cells. The cDNA library was prepared by purifying mast cell poly(A+)RNA (mRNA) and then enzymatically synthesizing double stranded complementary DNA (cDNA) copies of the mRNA. Synthetic adaptor oligonucleotides were ligated onto the ends of the cDNA enabling its insertion into the lambda vector using the Uni-ZAP vector system (Stratagene).

BMARNOT02

Bone marrow poly (A+) RNA, derived from a pooled sample of bone marrow from the breast bones of 24 males and females whose ages ranged from 16 to 70 years, was obtained from Clontech Laboratories Inc. (catalogue #6573-1 and #6573-2). The cDNA library was custom constructed by Stratagene essentially as follows. cDNA synthesis was primed using both oligo d(T) and random hexamers, and the two cDNA libraries were treated separately. Synthetic adapter oligonucleotides were ligated onto cDNA ends enabling its insertion into the Stratagene Uni-ZAP vector system. Finally, the two cDNA libraries were combined into a single library by mixing equal numbers of bacteriophage. The PBLUESCRIPT phagemid (Stratagene) was excised and transfected into E. coli host strain XL1-BLUE (Stratagene).

THP1PLB01

THP-1 is a human leukemic cell line derived from the blood of a 1-year-old boy with acute monocytic leukemia. Cells used for the PMA+LPS library (THP1PLB01) were cultured for 48 hr with 100 nm PMA in DMSO and for 4 hr with 1 $\mu$g/ml LPS. The PMA+LPS-stimulated cells represent activated macrophages. The cDNA library was custom constructed by Stratagene essentially as described below.

Stratagene prepared the cDNA library using oligo d(T) priming. Synthetic adapter oligonucleotides were ligated onto the cDNA molecules enabling them to be inserted into the UNI-ZAP vector system (Stratagene). The PBLUESCRIPT phagemid (Stratagene) was excised and transfected into E. coli host strain XL1-BLUE (Stratagene).

II Isolation and Sequencing of cDNA Clones

The phagemid forms of individual cDNA clones were obtained by the in vivo excision process, in which the host bacterial strain was co-infected with both the library phage and an f1 helper phage. Enzymes derived from both the library-containing phage and the helper phage nicked the DNA, initiated new DNA synthesis from defined sequences on the target DNA, and created a smaller, single stranded circular phagemid DNA molecule that included all DNA sequences of the PBLUESCRIPT phagemid and the cDNA insert. The phagemid DNA was released from the cells, purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was released from cells and purified using the Miniprep Kit (Cat. No. 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. No. 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R at 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying phagemid DNA include the use of MAGIC MINIPREPS™ DNA Purification System (Cat. No. A7100, Promega) or QIAWELL-8 Plasmid, QIAWELL PLUS DNA, and QIAWELL ULTRA DNA purification systems (Qiagen, Inc.).

The cDNAs were sequenced by the method of Sanger F. and A. R. Coulson (1975; J. Mol. Biol. 94:441f), using a Catalyst 800 (Perkin Elmer) or Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in the GenBank and EMBL databases using two homology search algorithms. The first algorithm was originally developed by Lipman D. J. and Pearson W. R. (1985; Science 227:1435). In this algorithm, the homologous regions are searched in a two-step manner. In the first step, highly homologous regions are determined by calculating a matching score using a homology score table. In this step, the parameter "Ktup" is used to establish a shifting, minimum window size for comparing two sequences. Ktup also sets the number of bases that must match to extract the highest homologous region among the sequences. In this step, no insertions or deletions are applied, and the homology is displayed as an initial (INIT) value.

In the second step, the homologous regions are aligned to obtain the highest matching score by inserting a gap when it is needed to accommodate a probable deletion. The matching score obtained in the first step is recalculated using the homology score table and the insertion score table to produce an optimized value.

DNA homologies between two sequences may also be examined graphically using the Harr method of constructing dot matrix homology plots (Needleman, S. B. and Wunsch, C. O. (1970) J. Mol. Biol. 48:443). This method produces a two-dimensional plot which can be useful in distinguishing between regions of homology and regions of repetition.

The second algorithm was developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul, S. F. et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding ZB occurs. Abundance and percent abundance are also reported. Abundance directly reflects the number of times a particular transcript is represented in a cDNA library, and percent abundance is abundance divided by the total number of sequences examined in the cDNA library.

V Extension of Polynucleotides Encoding ZB to Full Length or to Recover Regulatory Sequences Polynucleotides encoding ZB (SEQ ID NO:2, SEQ ID NO:4, or SEQ ID NO:6) are used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence outward, generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK Kit (Qiagen Inc.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2x Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

| | |
|---|---|
| Step 1 | 940 C for 60 sec |
| Step 2 | 94° C. for 20 sec |
| Step 3 | 65° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 $\mu$Ci of [-$\gamma^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots, or after the blots are exposed to a Phosphoimager cassette (Molecular Dynamics, Sunnyvale, Calif.), hybridization patterns are compared visually.

VII Antisense Molecules

Antisense molecules to the sequence encoding ZB, or any part thereof, is used to inhibit in vivo or in vitro expression of naturally occurring ZB. Although use of antisense oligonucleotides, comprising about 20 base-pairs, is specifically described, essentially the same procedure is used with larger cDNA fragments. An oligonucleotide based on the sequences encoding ZB is used to inhibit expression of naturally occurring ZB. The complementary oligonucleotide is designed from the most unique 5' sequence as shown and used either to inhibit transcription by preventing promoter binding to the upstream nontranslated sequence or translation of a transcript encoding ZB by preventing the ribosome from binding. Using an appropriate portion of the signal and 5' sequence of SEQ ID NO:2, SEQ ID NO:4, or SEQ ID NO:6, an effective antisense oligonucleotide includes any 15–20 nucleotides spanning the region which translates into the signal or 5' coding sequence of the polypeptide as shown in FIGS. 1A, 1B, 2A, 2B, 2C, 3A, 3B and 3C.

VIII Expression of ZB

Expression of ZB is accomplished by subcloning the cDNAs into appropriate vectors and transforming the vectors into host cells. In this case, the cloning vector, PSPORT, previously used for the generation of the cDNA library is used to express ZB in *E. coli*. Upstream of the cloning site, this vector contains a promoter for $\beta$-galactosidase, followed by sequence containing the amino-terminal Met, and the subsequent seven residues of $\beta$-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of $\beta$-galactosidase, about 5 to 15 residues of linker, and the full length protein. The signal residues direct the secretion of ZB into the bacterial growth media which can be used directly in the following assay for activity.

IX Demonstration of ZB Activity

The binding of $Zn^{2+}$ to ZB is assayed by monitoring the resulting changes in enthalpy (heat production or absorption) in an isothermal titration microcalorimeter (Micro-Cal Inc., Northampton, Mass.). Titration microcalorimetry measurements do not require labeling of the ligand or receptor molecules; detection is based solely on the intrinsic change in the heat of enthalpy upon binding. Multiple computer-controlled injections of a known volume of $ZnCl_2$ solution are directed into a thermally-controlled chamber containing ZB. The change in enthalpy after each injection is plotted against the number of injections to produce a binding isotherm. The volumes and concentrations of the injected $ZnCl_2$ solution and of the ZB solution are used along with the binding isotherm to calculate values for the number, affinity, and association constant of ZB with the $Zn^{2+}$ ligand.

X Production of ZB Specific Antibodies

ZB that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using DNASTAR software (DNASTAR Inc.) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring ZB Using Specific Antibodies

Naturally occurring or recombinant ZB is substantially purified by immunoaffinity chromatography using antibodies specific for ZB. An immunoaffinity column is constructed by covalently coupling ZB antibody to an activated chromatographic resin, such as CnBr-activated Sepharose (Pharmacia & Upjohn). After the coupling, the resin is blocked and washed according to the manufacturer's instructions.

Media containing ZB is passed over the immunoaffinity column, and the column is washed under conditions that allow the preferential absorbance of ZB (e.g., high ionic strength buffers in the presence of detergent). The column is eluted under conditions that disrupt antibody/ZB binding (eg, a buffer of pH 2–3 or a high concentration of a chaotrope, such as urea or thiocyanate ion), and ZB is collected.

XII Identification of Molecules Which Interact with ZB

ZB or biologically active fragments thereof are labeled with $^{125}$I Bolton-Hunter reagent (Bolton, A. E. and W. M. Hunter (1973) Biochem. J. 133:529–39). Candidate molecules previously arrayed in the wells of a multi-well plate are incubated with the labeled ZB, washed and any wells with labeled ZB complex are assayed. Data obtained using different concentrations of ZB are used to calculate values for the number, affinity, and association of ZB with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide sequence encoding a polypeptide comprising the amino acid sequence of SEQ ID NO:1.

2. A hybridization probe consisting of the polynucleotide sequence of claim 1.

3. An isolated and purified polynucleotide sequence consisting of SEQ ID NO:2.

4. An isolated and purified polynucleotide sequence which is complementary to the polynucleotide sequence of claim 1.

5. A hybridization probe consisting of the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1, the method comprising the steps of:

a) culturing the host cell of claim 7 under conditions suitable for the expression of the polypeptide; and b) recovering the polypeptide from the host cell culture.

* * * * *

Disclaimer

5,861,495—Jennifer L. Hillman; Janice Au-Young; Roger Coleman; Surya K. Goli, all of Palo Alto, Calif. HUMAN ZINC BINDING PROTEINS Patent date Jan. 19, 1999. Disclaimer filed Mar. 29, 2004, by the assignee, Incyte Pharmaceuticals, Inc.

Hereby enters this disclaimer to claims 1-8, of said patent.

*(Official Gazette, January 9, 2007)*

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 144 amino acids
( B ) TYPE: amino acid
( C ) STRANDEDNESS: single
( D ) TOPOLOGY: linear ( x i ) SEQUENCE DESCRIPTION: SEQ ID NO:1:

```
Met Pro Lys Val Lys Arg Ser Arg Lys Ala Pro Pro Asp Gly Trp Glu
 1               5                  10                  15

Leu Ile Glu Pro Thr Leu Asp Glu Leu Asp Gln Lys Met Arg Glu Ala
            20                  25                  30

Glu Thr Glu Pro His Glu Gly Lys Arg Lys Val Glu Ser Leu Trp Pro
        35                  40                  45

Ile Phe Arg Ile His His Gln Lys Thr Arg Tyr Ile Phe Asp Leu Phe
    50                  55                  60

Tyr Lys Arg Lys Ala Ile Ser Arg Glu Leu Tyr Glu Tyr Cys Ile Lys
65                  70                  75                  80

Glu Gly Tyr Ala Asp Lys Asn Leu Ile Ala Lys Trp Lys Lys Gln Gly
                85                  90                  95

Tyr Glu Asn Leu Cys Cys Leu Arg Cys Ile Gln Thr Arg Asp Thr Asn
            100                 105                 110

Phe Gly Thr Asn Cys Ile Cys Arg Val Pro Lys Ser Lys Leu Glu Val
        115                 120                 125

Gly Arg Ile Ile Glu Cys Thr His Cys Gly Cys Arg Gly Cys Ser Gly
    130                 135                 140
```

( 2 ) INFORMATION FOR SEQ ID NO:2:

( i ) SEQUENCE CHARACTERISTICS:
( A ) LENGTH: 828 base pairs
( B ) TYPE: nucleic acid
( C ) STRANDEDNESS: single
( D ) TOPOLOGY: linear ( x i ) SEQUENCE DESCRIPTION: SEQ ID NO:2:

| | | | | | |
|---|---|---|---|---|---|
| GCCTGAAGAG | CGGAAGCCTT | CTGTCGAGAA | GCAGCTACCC | AAGCTCCAGG | AGCTTCCGAA | 60 |
| GAAACAGGAC | CAGAGAGGGA | AGGTGACCTG | AAAGTCACAG | AATAATTTTT | TAGAGCTGAA | 120 |
| CAAGAATCCA | AGCCTGCAAC | TGCAGAGACG | AGAGATCTTT | CTGCTGTCTA | TACTCTTGGA | 180 |
| AAGCACATCC | TAAGATCTTT | GCAGATTATC | CTGTGGAAGG | AAAATGCCTA | AAGTCAAAAG | 240 |
| AAGCCGGAAA | GCACCCCCAG | ATGGCTGGGA | GTTGATTGAG | CCAACACTGG | ATGAATTAGA | 300 |
| TCAAAAGATG | AGAGAAGCTG | AAACAGAACC | GCATGAGGGA | AAGAGGAAAG | TGGAATCTCT | 360 |
| GTGGCCCATC | TTCAGGATCC | ACCACCAGAA | AACCCGCTAC | ATCTTCGACC | TCTTTTACAA | 420 |
| GCGGAAAGCC | ATCAGCAGAG | AACTCTATGA | ATATTGTATT | AAAGAAGGCT | ATGCAGACAA | 480 |
| AAACCTGATT | GCAAAATGGA | AAAGCAAGG | ATATGAGAAC | TTGTGCTGCC | TGCGGTGCAT | 540 |
| TCAGACACGG | GACACCAACT | TCGGGACGAA | CTGCATCTGC | CGCGTGCCCA | AAAGCAAGCT | 600 |
| GGAAGTGGGC | CGCATCATCG | AGTGCACACA | CTGTGGCTGT | CGTGGCTGCT | CTGGCTGAGG | 660 |
| CTGGCGCGCT | CCACCCTGGA | CTCTGGACTT | CGCAGGTTCC | TGCCTGTCAC | GCCACCCCT | 720 |
| TCCTGGGAGC | AGCGAGCAGT | GCCCCAGGCC | CGAGTTGGAG | CACGGTCTCT | ATGGGGAAGG | 780 |
| CTTCGCTGTC | TATCAGCTGT | GATTTGTAAA | AATAAAATCT | TTAAATCT | | 828 |

( 2 ) INFORMATION FOR SEQ ID NO:3:

( i ) SEQUENCE CHARACTERISTICS:
        ( A ) LENGTH: 180 amino acids
        ( B ) TYPE: amino acid
        ( C ) STRANDEDNESS: single
        ( D ) TOPOLOGY: linear ( x i ) SEQUENCE DESCRIPTION: SEQ ID NO:3:

```
Met  Ala  Ala  Ala  Glu  Glu  Glu  Asp  Gly  Gly  Pro  Glu  Gly  Pro  Asn  Arg
 1             5                  10                 15

Glu  Arg  Gly  Gly  Ala  Gly  Ala  Thr  Phe  Glu  Cys  Asn  Ile  Cys  Leu  Glu
              20                 25                 30

Thr  Ala  Arg  Glu  Ala  Val  Val  Ser  Val  Cys  Gly  His  Leu  Tyr  Cys  Trp
         35                 40                 45

Pro  Cys  Leu  His  Gln  Trp  Leu  Glu  Thr  Arg  Pro  Glu  Arg  Gln  Glu  Cys
     50                 55                 60

Pro  Val  Cys  Lys  Ala  Gly  Ile  Ser  Arg  Glu  Lys  Val  Val  Pro  Leu  Tyr
65                  70                 75                 80

Gly  Arg  Gly  Ser  Gln  Lys  Pro  Gln  Asp  Pro  Arg  Leu  Lys  Thr  Pro  Pro
                 85                 90                 95

Arg  Pro  Gln  Gly  Gln  Arg  Pro  Ala  Pro  Glu  Ser  Arg  Gly  Gly  Phe  Gln
             100                105                110

Pro  Phe  Gly  Asp  Thr  Gly  Gly  Phe  His  Phe  Ser  Phe  Gly  Val  Gly  Ala
         115                120                125

Phe  Pro  Phe  Gly  Phe  Phe  Thr  Thr  Val  Phe  Asn  Ala  His  Glu  Pro  Phe
     130                135                140

Arg  Arg  Gly  Thr  Gly  Val  Asp  Leu  Gly  Gln  Gly  His  Pro  Ala  Ser  Ser
145                 150                155                160

Trp  Gln  Asp  Ser  Leu  Phe  Leu  Phe  Leu  Ala  Ile  Phe  Phe  Phe  Trp
                 165                170                175

Leu  Leu  Ser  Ile
             180
```

( 2 ) INFORMATION FOR SEQ ID NO:4:

(i) SEQUENCE CHARACTERISTICS:
  (A) LENGTH: 944 base pairs
  (B) TYPE: nucleic acid
  (C) STRANDEDNESS: single
  (D) TOPOLOGY: linear (xi) SEQUENCE DESCRIPTION: SEQ ID NO:4:

```
CAACGATCGT GGGCAGGAGG TGGTTTCTGG TTTGTTGGGG CGTGTGTATG TGTATTTGGG    60
GGGACTGAAG GGTACGTGGG GCGAAACAAA ACCGGCCATG GCAGCAGCGG AGGAGGAGGA   120
CGGGGGCCCC GAAGGGCCAA ATCGCGAGCG GGGCGGGGCG GGCGCGACCT TCGAATGTAA   180
TATATGTTTG GAGACTGCTC GGGAAGCTGT GGTCAGTGTG TGTGGCCACC TGTACTGTTG   240
GCCATGTCTT CATCAGTGGC TGGAGACACG GCCAGAACGG CAAGAGTGTC CAGTATGTAA   300
AGCTGGGATC AGCAGAGAGA AGGTTGTCCC GCTTTATGGG CGAGGGAGCC AGAAGCCCCA   360
GGATCCCAGA TTAAAAACTC CACCCCGCCC CCAGGGCCAG AGACCAGCTC CGGAGAGCAG   420
AGGGGGATTC CAGCCATTTG GTGATACCGG GGGCTTCCAC TTCTCATTTG GTGTTGGTGC   480
TTTTCCCTTT GGCTTTTTCA CCACCGTCTT CAATGCCCAT GAGCCTTTCC GCCGGGGTAC   540
AGGTGTGGAT CTGGGACAGG GTCACCCAGC CTCCAGCTGG CAGGATTCCC TCTTCCTGTT   600
TCTCGCCATC TTCTTCTTTT TTTGGCTGCT CAGTATTTGA GCTATGTCTG CTTCCTGCCC   660
ACCTCCAGCC AGAGAAGAAT CAGTATATTG AAGGTCCCTG CTGAMCCTTC CGTATCCTGG   720
AACCCCTGAC CCTCTTTTTT TTTTGCTAAN GGCACCCTGA ACTTTTCCNG AAGGCTGGGA   780
AAAAATTAAT CTTTCTTAAT GGAAANCTCT CCCCAAGNCC TCATAACTTT TTAATCCCCC   840
CNGGGAAGAG ATGAATAAAA AATTNTTCNC CCCCAATTTT GCTTCCCGAT TCTNATTNAC   900
TCAAGTGGCA ATTCCCTNAT CTCCCCTCCA CTTTGATAAT TATT                    944
```

(2) INFORMATION FOR SEQ ID NO:5:

(i) SEQUENCE CHARACTERISTICS:
    (A) LENGTH: 276 amino acids
    (B) TYPE: amino acid
    (C) STRANDEDNESS: single
    (D) TOPOLOGY: linear (xi) SEQUENCE DESCRIPTION: SEQ ID NO:5:

```
Met Thr His Pro Gly Thr Gly Asp Ile Ile Ala Val Met Ile Thr Glu
 1               5                  10                  15

Leu Arg Gly Lys Asp Ile Leu Ser Tyr Leu Glu Lys Asn Ile Ser Val
                20                  25                  30

Gln Met Thr Ile Ala Val Gly Thr Arg Met Pro Pro Lys Asn Phe Ser
            35                  40                  45

Arg Gly Ser Leu Val Phe Val Ser Ile Ser Phe Ile Val Leu Met Ile
        50                  55                  60

Ile Ser Ser Ala Trp Leu Ile Phe Tyr Phe Ile Gln Lys Ile Arg Tyr
65                  70                  75                  80

Thr Asn Ala Arg Asp Arg Asn Gln Arg Arg Leu Gly Asp Ala Ala Lys
                85                  90                  95

Lys Ala Ile Ser Lys Leu Thr Thr Arg Thr Val Lys Lys Gly Asp Lys
                100                 105                 110

Glu Thr Asp Pro Asp Phe Asp His Cys Ala Val Cys Ile Glu Ser Tyr
            115                 120                 125

Lys Gln Asn Asp Val Val Arg Ile Leu Pro Cys Lys His Val Phe His
        130                 135                 140

Lys Ser Cys Val Asp Pro Trp Leu Ser Glu His Cys Thr Cys Pro Met
145                 150                 155                 160
```

| | | | | | | | | | | | | | | |
|---|---|---|---|---|---|---|---|---|---|---|---|---|---|---|
| Cys | Lys | Leu | Asn | Ile<br>165 | Leu | Lys | Ala | Leu | Gly<br>170 | Ile | Val | Pro | Asn | Leu<br>175 | Pro |
| Cys | Thr | Asp | Asn<br>180 | Val | Ala | Phe | Asp | Met<br>185 | Glu | Arg | Leu | Thr | Arg<br>190 | Thr | Gln |
| Ala | Val | Asn<br>195 | Arg | Arg | Ser | Ala | Leu<br>200 | Gly | Asp | Leu | Ala | Gly<br>205 | Asp | Asn | Ser |
| Leu | Gly<br>210 | Leu | Glu | Pro | Leu | Arg<br>215 | Thr | Ser | Gly | Ile | Ser<br>220 | Pro | Leu | Pro | Gln |
| Asp<br>225 | Gly | Glu | Leu | Thr | Pro<br>230 | Arg | Thr | Gly | Glu | Ile<br>235 | Asn | Ile | Ala | Val | Thr<br>240 |
| Lys | Glu | Trp | Phe | Ile<br>245 | Ile | Ala | Ser | Phe | Gly<br>250 | Leu | Leu | Ser | Ala | Leu<br>255 | Thr |
| Leu | Cys | Tyr | Met<br>260 | Ile | Ile | Arg | Ala | Thr<br>265 | Ala | Ser | Leu | Asn | Ala<br>270 | Asn | Glu |
| Val | Glu | Trp | Phe<br>275 | | | | | | | | | | | | |

( 2 ) INFORMATION FOR SEQ ID NO:6:

( i ) SEQUENCE CHARACTERISTICS:
      ( A ) LENGTH: 1253 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

| | | | | | |
|---|---|---|---|---|---|
| GNCGCTAACG | GGCTTGANTC | CCCCAAGGCC | GAGGTCCGCG | GCCAGGTGCT | GGCGCCGCTG | 60 |
| CCCCTCCACG | GAGTTGCTGA | TCATCTGGGC | TGTGATCCAC | AAACCCGGTT | CTTTGTCCCT | 120 |
| CCTAATATCA | AACAGTGGAT | TGCCTTGCTG | CAGAGGGGAA | ACTGCACGTT | TAAAGAGAAA | 180 |
| ATATCACGGG | CCGCTTTCCA | CAATGCAGTT | GCTGTAGTCA | TCTACAATAA | TAAATCCAAA | 240 |
| GAGGAGCCAG | TTACCATGAC | TCATCCAGGC | ACTGGAGATA | TTATTGCTGT | CATGATAACA | 300 |
| GAATTGAGGG | GTAAGGATAT | TTTGAGTTAT | CTGGAGAAAA | ACATCTCTGT | ACAAATGACA | 360 |
| ATAGCTGTTG | GAACTCGAAT | GCCACCGAAG | AACTTCAGCC | GTGGCTCTCT | AGTCTTCGTG | 420 |
| TCAATATCCT | TTATTGTTTT | GATGATTATT | TCTTCAGCAT | GGCTCATATT | CTACTTCATT | 480 |
| CAGAAGATCA | GGTACACAAA | TGCACGCGAC | AGGAACCAGC | GTCGTCTCGG | AGATGCAGCC | 540 |
| AAGAAAGCCA | TCAGTAAATT | GACAACCAGG | ACAGTAAAGA | AGGGTGACAA | GGAAACTGAC | 600 |
| CCAGACTTTG | ATCATTGTGC | AGTCTGCATA | GAGAGCTATA | AGCAGAATGA | TGTCGTCCGA | 660 |
| ATTCTCCCCT | GCAAGCATGT | TTTCCACAAA | TCCTGCGTGG | ATCCCTGGCT | TAGTGAACAT | 720 |
| TGTACCTGTC | CTATGTGCAA | ACTTAATATA | TTGAAGGCCC | TGGGAATTGT | GCCGAATTTG | 780 |
| CCATGTACTG | ATAACGTAGC | ATTCGATATG | GAAAGGCTCA | CCAGAACCCA | AGCTGTTAAC | 840 |
| CGAAGATCAG | CCCTCGGCGA | CCTCGCCGGC | GACAACTCCC | TTGGCCTTGA | GCCACTTCGA | 900 |
| ACTTCGGGGA | TCTCACCTCT | TCCTCAGGAT | GGGGAGCTCA | CTCCGAGAAC | AGGAGAAATC | 960 |
| AACATTGCAG | TAACAAAAGA | ATGGTTTATT | ATTGCCAGTT | TTGGCCTCCT | CAGTGCCCTC | 1020 |
| ACACTCTGCT | ACATGATCAT | CAGAGCCACA | GCTAGCTTGA | ATGCTAATGA | GGTAGAATGG | 1080 |
| TTTTGAAGAA | GAAAAAACCT | GCTTTCTGAC | TGATTTTGCC | TTGAAGGAAA | AAGAACCTA | 1140 |
| TTTTTGTGCA | TCATTTACCA | ATCATGCCAC | ACAAGCATTT | ATTTTAGTA | CATTTTATTT | 1200 |
| TTTCATAAAA | TTGCTAATGC | CAAAGGTTTG | TATTAAAAGG | GATAAATAGT | AAA | 1253 |

( 2 ) INFORMATION FOR SEQ ID NO:7:

(i) SEQUENCE CHARACTERISTICS:
(A) LENGTH: 144 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 120625

(xi) SEQUENCE DESCRIPTION: SEQ ID NO:7:

```
Met Pro Lys Val Lys Arg Ser Arg Lys Pro Pro Asp Gly Trp Glu
 1               5                  10                 15

Leu Ile Glu Pro Thr Leu Asp Glu Leu Asp Gln Lys Met Arg Glu Ala
                20                  25                 30

Glu Thr Asp Pro His Glu Gly Lys Arg Lys Val Glu Ser Leu Trp Pro
            35                  40                 45

Ile Phe Arg Ile His His Gln Lys Thr Arg Tyr Ile Phe Asp Leu Phe
        50                  55                 60

Tyr Lys Arg Lys Ala Ile Ser Arg Glu Leu Tyr Asp Tyr Cys Ile Arg
 65                 70                  75                 80

Glu Gly Tyr Ala Asp Lys Asn Leu Ile Ala Lys Trp Lys Lys Gln Gly
                85                  90                 95

Tyr Glu Asn Leu Cys Cys Leu Arg Cys Ile Gln Thr Arg Asp Thr Asn
               100                 105                110

Phe Gly Thr Asn Cys Ile Cys Arg Val Pro Lys Thr Lys Leu Glu Val
           115                 120                125

Gly Arg Ile Ile Glu Cys Thr His Cys Gly Cys Arg Gly Cys Ser Gly
       130                 135                140
```

(2) INFORMATION FOR SEQ ID NO:8:

(i) SEQUENCE CHARACTERISTICS:
(A) LENGTH: 326 amino acids
(B) TYPE: amino acid
(C) STRANDEDNESS: single
(D) TOPOLOGY: linear (vii) IMMEDIATE SOURCE:
(A) LIBRARY: GenBank
(B) CLONE: 461632

(xi) SEQUENCE DESCRIPTION: SEQ ID NO:8:

```
Met His Arg Thr Thr Arg Ile Lys Ile Thr Glu Leu Asn Pro His Leu
 1               5                  10                 15

Met Cys Val Leu Cys Gly Gly Tyr Phe Ile Asp Ala Thr Thr Ile Ile
                20                  25                 30

Glu Cys Leu His Ser Phe Cys Lys Thr Cys Ile Val Arg Tyr Leu Glu
            35                  40                 45

Thr Ser Lys Tyr Cys Pro Ile Cys Asp Val Gln Val His Lys Thr Arg
 50                 55                  60

Pro Leu Leu Asn Ile Arg Ser Asp Lys Thr Leu Gln Asp Ile Val Tyr
 65                 70                  75                 80

Lys Leu Val Pro Gly Leu Phe Lys Asn Glu Met Lys Arg Arg Arg Asp
                85                  90                 95

Phe Tyr Ala Ala His Pro Ser Ala Asp Ala Ala Asn Gly Ser Asn Glu
           100                 105                110

Asp Arg Gly Glu Val Ala Asp Glu Asp Lys Arg Ile Ile Thr Asp Asp
           115                 120                125

Glu Ile Ile Ser Leu Ser Ile Glu Phe Phe Asp Gln Asn Arg Leu Asp
```

|  |  |  | 130 |  |  |  | 135 |  |  |  | 140 |  |  |
|---|---|---|---|---|---|---|---|---|---|---|---|---|---|
| Arg | Lys | Val | Asn | Lys | Asp | Lys | Glu | Lys | Ser | Lys | Glu | Glu | Val | Asn | Asp |
| 145 |   |   |   |   | 150 |   |   |   |   | 155 |   |   |   |   | 160 |
| Lys | Arg | Tyr | Leu | Arg | Cys | Pro | Ala | Ala | Met | Thr | Val | Met | His | Leu | Arg |
|   |   |   |   | 165 |   |   |   |   | 170 |   |   |   |   | 175 |   |
| Lys | Phe | Leu | Arg | Ser | Lys | Met | Asp | Ile | Pro | Asn | Thr | Phe | Gln | Ile | Asp |
|   |   |   | 180 |   |   |   |   | 185 |   |   |   |   | 190 |   |   |
| Val | Met | Tyr | Glu | Glu | Glu | Pro | Leu | Lys | Asp | Tyr | Tyr | Thr | Leu | Met | Asp |
|   |   | 195 |   |   |   |   | 200 |   |   |   |   | 205 |   |   |   |
| Ile | Ala | Tyr | Ile | Tyr | Thr | Trp | Arg | Arg | Asn | Gly | Pro | Leu | Pro | Leu | Lys |
|   | 210 |   |   |   |   | 215 |   |   |   |   | 220 |   |   |   |   |
| Tyr | Arg | Val | Arg | Pro | Thr | Cys | Lys | Arg | Met | Lys | Ile | Ser | His | Gln | Arg |
| 225 |   |   |   |   | 230 |   |   |   |   | 235 |   |   |   |   | 240 |
| Asp | Gly | Leu | Thr | Asn | Ala | Gly | Glu | Leu | Glu | Ser | Asp | Ser | Gly | Ser | Asp |
|   |   |   |   | 245 |   |   |   |   | 250 |   |   |   |   | 255 |   |
| Lys | Ala | Asn | Ser | Pro | Ala | Gly | Gly | Val | Pro | Ser | Thr | Ser | Ser | Cys | Leu |
|   |   |   | 260 |   |   |   |   | 265 |   |   |   |   | 270 |   |   |
| Pro | Ser | Pro | Ser | Thr | Pro | Val | Gln | Ser | Pro | His | Pro | Gln | Phe | Pro | His |
|   |   | 275 |   |   |   |   | 280 |   |   |   |   | 285 |   |   |   |
| Ile | Ser | Ser | Thr | Met | Asn | Gly | Thr | Ser | Asn | Ser | Pro | Ser | Gly | Asn | His |
|   | 290 |   |   |   |   | 295 |   |   |   |   | 300 |   |   |   |   |
| Gln | Ser | Ser | Phe | Ala | Asn | Arg | Pro | Arg | Lys | Ser | Ser | Val | Asn | Gly | Ser |
| 305 |   |   |   |   | 310 |   |   |   |   | 315 |   |   |   |   | 320 |
| Ser | Ala | Thr | Ser | Ser | Gly |  |  |  |  |  |  |  |  |  |  |
|   |   |   |   | 325 |   |  |  |  |  |  |  |  |  |  |  |

( 2 ) INFORMATION FOR SEQ ID NO:9:

( i ) SEQUENCE CHARACTERISTICS:
        ( A ) LENGTH: 284 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 157535

( x i ) SEQUENCE DESCRIPTION: SEQ ID NO:9:

| Met | Gln | Leu | Glu | Lys | Met | Gln | Ile | Lys | Gly | Lys | Thr | Arg | Asn | Ile | Ala |
|---|---|---|---|---|---|---|---|---|---|---|---|---|---|---|---|
| 1 |   |   |   | 5 |   |   |   |   | 10 |   |   |   |   | 15 |   |
| Ala | Val | Ile | Thr | Tyr | Gln | Asn | Ile | Gly | Gln | Asp | Leu | Ser | Leu | Thr | Leu |
|   |   |   | 20 |   |   |   |   | 25 |   |   |   |   | 30 |   |   |
| Asp | Lys | Gly | Tyr | Asn | Val | Thr | Ile | Ser | Ile | Ile | Glu | Gly | Arg | Arg | Gly |
|   |   | 35 |   |   |   |   | 40 |   |   |   |   | 45 |   |   |   |
| Val | Arg | Thr | Ile | Ser | Ser | Leu | Asn | Arg | Thr | Ser | Val | Leu | Phe | Val | Ser |
|   | 50 |   |   |   |   | 55 |   |   |   |   | 60 |   |   |   |   |
| Ile | Ser | Phe | Ile | Val | Asp | Asp | Ile | Leu | Cys | Trp | Leu | Ile | Phe | Tyr | Tyr |
| 65 |   |   |   |   | 70 |   |   |   |   | 75 |   |   |   |   | 80 |
| Ile | Gln | Arg | Phe | Arg | Tyr | Met | Gln | Ala | Lys | Asp | Gln | Gln | Ser | Arg | Asn |
|   |   |   |   | 85 |   |   |   |   | 90 |   |   |   |   | 95 |   |
| Leu | Cys | Ser | Val | Thr | Lys | Lys | Ala | Ile | Met | Lys | Ile | Pro | Thr | Lys | Thr |
|   |   |   | 100 |   |   |   |   | 105 |   |   |   |   | 110 |   |   |
| Gly | Lys | Phe | Ser | Asp | Glu | Lys | Asp | Leu | Asp | Ser | Asp | Cys | Cys | Ala | Ile |
|   |   | 115 |   |   |   |   | 120 |   |   |   |   | 125 |   |   |   |
| Cys | Ile | Glu | Ala | Tyr | Lys | Pro | Thr | Asp | Thr | Ile | Arg | Ile | Leu | Pro | Cys |
|   | 130 |   |   |   |   | 135 |   |   |   |   | 140 |   |   |   |   |

-continued

| | | | | | | | | | | | | | | | |
|---|---|---|---|---|---|---|---|---|---|---|---|---|---|---|---|
| Lys 145 | His | Glu | Phe | His | Lys 150 | Asn | Cys | Ile | Asp | Pro 155 | Trp | Leu | Ile | Glu | His 160 |
| Arg | Thr | Cys | Pro | Met 165 | Cys | Lys | Leu | Asp | Val 170 | Leu | Lys | Phe | Tyr | Gly 175 | Tyr |
| Val | Val | Gly | Asp 180 | Gln | Ile | Tyr | Gln | Thr 185 | Pro | Ser | Pro | Gln | His 190 | Thr | Ala |
| Pro | Ile | Ala 195 | Ser | Ile | Glu | Glu | Val 200 | Pro | Val | Ile | Val | Val 205 | Ala | Val | Pro |
| His | Gly 210 | Pro | Gln | Pro | Leu | Gln 215 | Pro | Leu | Gln | Ala | Ser 220 | Asn | Met | Ser | Ser |
| Phe 225 | Ala | Pro | Ser | His | Tyr 230 | Phe | Gln | Ser | Ser | Arg 235 | Ser | Pro | Ser | Ser | Ser 240 |
| Val | Gln | Gln | Gln | Leu 245 | Ala | Pro | Leu | Thr | Tyr 250 | Gln | Pro | His | Pro | Gln 255 | Gln |
| Ala | Ala | Ser | Glu 260 | Arg | Gly | Arg | Arg | Asn 265 | Ser | Ala | Pro | Ala | Thr 270 | Met | Pro |
| His | Ala | Ile 275 | Thr | Ala | Ser | His | Gln 280 | Val | Thr | Asp | Val | | | | |